(12) United States Patent
Abe et al.

(10) Patent No.: US 7,883,786 B2
(45) Date of Patent: Feb. 8, 2011

(54) BIPHENYL DERIVATIVE AND ORGANIC LIGHT-EMITTING ELEMENT USING SAME

(75) Inventors: Shigemoto Abe, Tokyo (JP); Akihiro Senoo, Kawasaki (JP); Jun Kamatani, Tokyo (JP); Satoshi Igawa, Fujisawa (JP); Naoki Yamada, Inagi (JP)

(73) Assignee: Canon Kabushiki Kaisha, Tokyo (JP)

( * ) Notice: Subject to any disclaimer, the term of this patent is extended or adjusted under 35 U.S.C. 154(b) by 380 days.

(21) Appl. No.: 12/060,388

(22) Filed: Apr. 1, 2008

(65) Prior Publication Data

US 2008/0297034 A1    Dec. 4, 2008

(30) Foreign Application Priority Data

Apr. 9, 2007    (JP) .............................. 2007-101489

(51) Int. Cl.
*H01L 51/52*  (2006.01)
*C07C 13/567*  (2006.01)
*C07F 5/02*  (2006.01)
*C07D 209/82*  (2006.01)

(52) U.S. Cl. ...................... 428/690; 428/917; 313/504; 313/506; 585/27; 568/6; 548/405

(58) Field of Classification Search ........................ None
See application file for complete search history.

(56) References Cited

U.S. PATENT DOCUMENTS 7,291,406 B2    11/2007    Thompson et al. .......... 428/690

(Continued)

OTHER PUBLICATIONS

Pina et al., J. Phys. Chem. B, (2008), vol. 112, pp. 1104-1111.*

(Continued)

*Primary Examiner*—Dawn Garrett
(74) *Attorney, Agent, or Firm*—Fitzpatrick, Cella, Harper & Scinto

(57) ABSTRACT

The invention provides a novel compound used as a material for organic light-emitting elements, and an organic light-emitting element which has highly efficient and highly luminescent optical power and is superior in durability. The organic light-emitting element includes an anode and a cathode, and a layer which contains an organic compound and is held between the anode and the cathode. The layer containing an organic compound includes a biphenyl derivative represented by the following general formula (1):

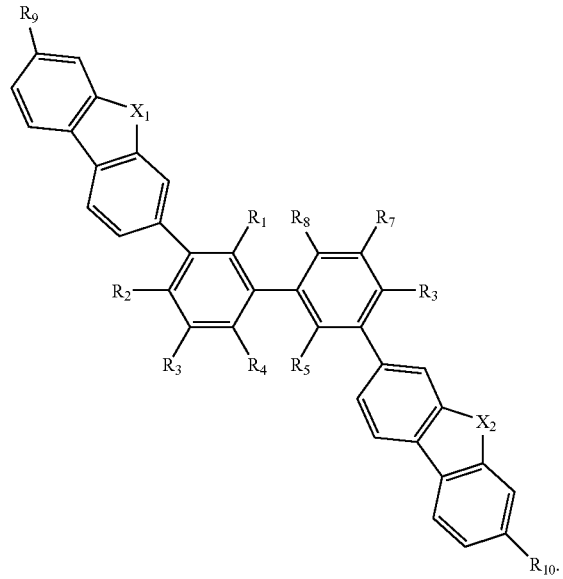

(1)

5 Claims, 3 Drawing Sheets

U.S. PATENT DOCUMENTS

| | | | |
|---|---|---|---|
| 2005/0244670 A1 | 11/2005 | Saitoh et al. | 428/690 |
| 2006/0051613 A1 | 3/2006 | Tomita et al. | 428/690 |
| 2006/0068221 A1 | 3/2006 | Saitoh et al. | 428/690 |
| 2007/0122652 A1 | 5/2007 | Hashimoto et al. | 428/690 |
| 2007/0128467 A1 | 6/2007 | Iwakuma et al. | 428/690 |
| 2007/0228399 A1 | 10/2007 | Iwawaki et al. | 257/89 |
| 2007/0228941 A1 | 10/2007 | Abe et al. | 313/504 |

OTHER PUBLICATIONS

O'Brien, et al. "Improved energy transfer in electrophosphorescent device"; Applied Physics Letters, vol. 74, No. 3, p. 442-444 (1999).

Baldo, et al. "Very high-efficency green organic light-emitting devices based on electrophosphorescence", Applied Physics Letters, vol. 75, No. 1, p. 4-6 (1999).

* cited by examiner

BIPHENYL DERIVATIVE AND ORGANIC LIGHT-EMITTING ELEMENT USING SAME

BACKGROUND OF THE INVENTION

1. Field of the Invention

This invention relates to a biphenyl derivative, and an organic light-emitting element using the biphenyl derivative.

2. Description of the Related Art

In recent years, dramatic progress has been made in organic light-emitting elements. As characteristic features thereof, it is noted that high luminance at low applied voltage, a variety of light emission wavelengths and quick response can be achieved, and light-emitting devices can be made thin and light-weight. Accordingly, such organic light-emitting elements are indicating possibilities for a wide range of uses.

Fluorescent organic compounds are contained in electron transport layers, light-emitting layers, etc. the organic light-emitting elements include. Such fluorescent organic compounds include aromatic compounds and condensed polycyclic aromatic compounds, and many studies have been made on these compounds. However, when fluorescent organic compounds having hitherto been proposed are used for organic light-emitting elements, it cannot be said that light-emitting elements having satisfactory light emission luminance and durability have been obtained.

Studies are recently being made not only on conventional light-emitting elements utilizing the fluorescence that is produced at the time of transition from the excited singlet state to the ground state, but also on organic light-emitting elements utilizing the light emission by phosphorescence via next triplet excitons. As specific examples, the following Non-patent Documents 1 and 2 may be given. In these specific examples, an organic light-emitting element is primarily used which is made up of a layer formed of organic compounds in four layers. Specifically, this organic light-emitting element has a hole transport layer, a light-emitting layer, an exciton diffusion preventive layer and an electron transport layer in this order from the anode side.

A compound is proposed which has as its basic skeleton biphenyl into which an aromatic compound or a heterocyclic compound has been introduced, and has been applied to organic light-emitting elements. As specific examples, the following Patent Documents 1 to 3 may be given.

Patent Document 1: WO2004/074399.
Patent Document 2: WO2005/063920.
Patent Document 3: US2006/0029829.
Non-patent Document 1: Improved energy transfer in electrophosphorescent device (D. F. O'Brien et al., Applied Physics Letters, Vol. 74, No. 3, p. 442 (1999).
Non-patent Document 2: Very high-efficiency green organic light-emitting devices based on electrophosphorescence (M. A. Baldo et al., Applied Physics Letters, Vol. 75, No. 1, p. 4 (1999).

In order to apply organic light-emitting elements to display devices, the organic light-emitting elements are required to have highly efficient and highly luminescent optical power and at the same time to ensure high durability. However, any organic light-emitting elements having hitherto been proposed cannot still be said to satisfactorily have resolved these problems.

SUMMARY OF THE INVENTION

An object of the present invention is to provide a novel compound used as a material for organic light-emitting elements. Another object of the present invention is to provide an organic light-emitting element having highly efficient and highly luminescent optical power and ensuring high durability. A further object of the present invention is to provide an organic light-emitting element which can be manufactured with ease and also can be produced at relatively low costs.

The present invention provides a biphenyl derivative represented by the following general formula (1):

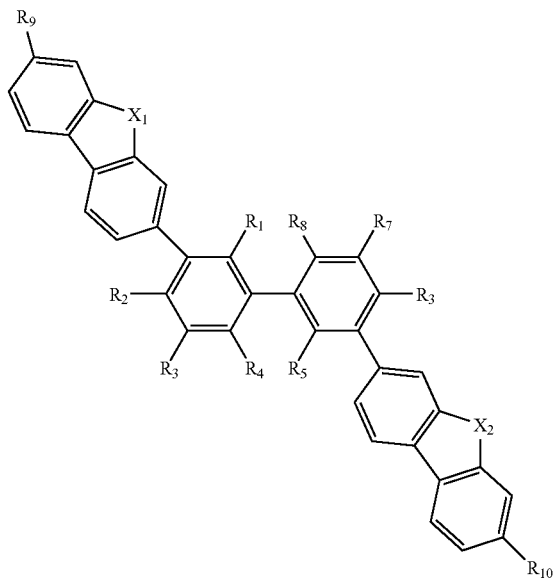

In the general formula (1), $R_1$, $R_2$, $R_4$ to $R_6$ and $R_8$ to $R_{10}$ each represent a hydrogen atom, a substituted or unsubstituted alkyl group, a substituted or unsubstituted aralkyl group, a substituted or unsubstituted alkenyl group, a substituted or unsubstituted alkynyl group or a substituted or unsubstituted alkoxyl group, and may be the same or different; $R_3$ and $R_7$ each represent a hydrogen atom, a substituted or unsubstituted alkyl group, a substituted or unsubstituted aryl group or a substituted or unsubstituted heterocyclic group, and may be the same or different; and $X_1$ and $X_2$ each represent —$CR_{11}R_{12}$— ($R_{11}$ and $R_{12}$ each represent a hydrogen atom, an alkyl group, a substituted or unsubstituted aralkyl group, a substituted or unsubstituted aryl group, a substituted or unsubstituted heterocyclic group or a halogen atom, and may be the same or different) or —$NR_{11}$—, and may be the same or different.

According to the present invention, a novel compound used as a material for organic light-emitting elements is provided. According to the present invention, an organic light-emitting element is provided having highly efficient and highly luminescent optical power and ensuring high durability. According to the present invention, an organic light-emitting element is provided which can be manufactured with ease and also can be produced at relatively low costs.

Further features of the present invention will become apparent from the following description of exemplary embodiments with reference to the accompanying drawings.

DESCRIPTION OF THE EMBODIMENTS

Figure 1:
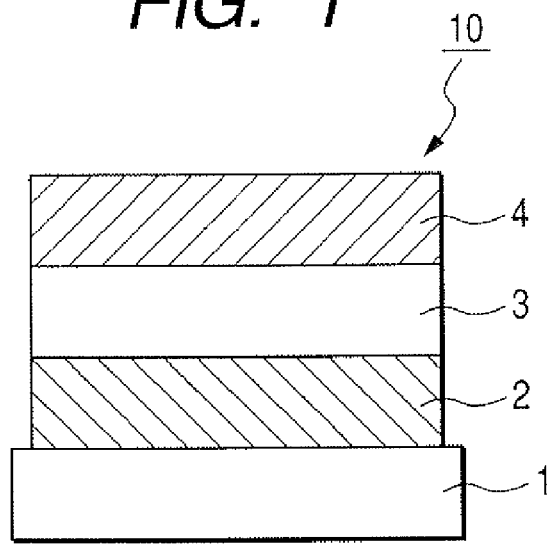
FIG. 1 is a sectional view showing a first embodiment in the organic light-emitting element of the present invention.

In the first place, the biphenyl derivative of the present invention will be described in detail. The biphenyl derivative of the present invention is represented by the following general formula (1):

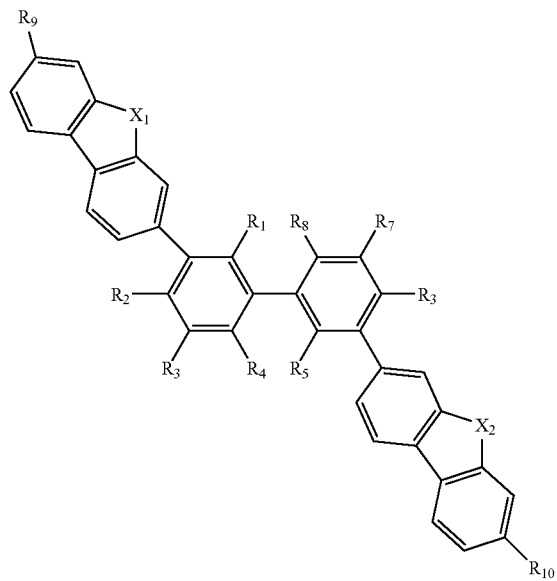

(1)

In the general formula (1), $R_1$, $R_2$, $R_4$ to $R_6$ and $R_8$ to $R_{10}$ each independently represent a hydrogen atom, a substituted or unsubstituted alkyl group, a substituted or unsubstituted aralkyl group, a substituted or unsubstituted alkenyl group, a substituted or unsubstituted alkynyl group or a substituted or unsubstituted alkoxyl group.

The alkyl group represented by $R_1$, $R_2$, $R_4$ to $R_6$ and $R_8$ to $R_{10}$ may include, but is not limited to, a methyl group, a methyl-d1 group, a methyl-d3 group, an ethyl group, an ethyl-d5 group, a n-propyl group, a n-butyl group, a n-pentyl group, a n-hexyl group, a n-heptyl group, a n-octyl group, a n-decyl group, an iso-propyl group, an iso-propyl-d7 group, an iso-butyl group, a sec-butyl group, a tert-butyl group, a tert-butyl-d9 group, an iso-pentyl group, a neopentyl group, a tert-octyl group, a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a 5-fluoropentyl group, a 6-fluorohexyl group, a chloromethyl group, a trichloromethyl group, a 2-chloroethyl group, a 2,2,2-trichloroethyl group, a 4-chlorobutyl group, a 5-chloropentyl group, a 6-chlorohexyl group, a bromomethyl group, a 2-bromoethyl group, an iodomethyl group, a 2-iodoethyl group, a hydroxymethyl group, a hydroxyethyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a norbornyl group and an adamantyl group.

The aralkyl group represented by $R_1$, $R_2$, $R_4$ to $R_6$ and $R_8$ to $R_{10}$ may include, but is not limited to, a benzyl group, a 2-phenylethyl group, a 2-phenylisopropyl group, a 1-naphtylmethyl group, a 2-naphtylmethyl group, a 2-(1-naphthyl)ethyl group, a 2-(2-naphthyl)ethyl group, a 9-anthrylmethyl group, a 2-(9-anthryl)ethyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group and a 4-bromobenzyl group.

The alkenyl group represented by $R_1$, $R_2$, $R_4$ to $R_6$ and $R_8$ to $R_{10}$ may include, but is not limited to, a vinyl group, an allyl group, a 2-propenyl group, a 1-propenyl group, an iso-propenyl group, a 1-butenyl group, a 2-butenyl group, a 3-butenyl group and a styryl group.

The alkynyl group represented by $R_1$, $R_2$, $R_4$ to $R_6$ and $R_8$ to $R_{10}$ may include, but is not limited to, an acetylenyl group, a phenylacetylenyl group and a 1-propynyl group.

The alkoxyl group represented by $R_1$, $R_2$, $R_4$ to $R_6$ and $R_8$ to $R_{10}$ may include alkyloxyl groups having any of the alkyl groups described above and aralkyloxyl groups having any of the aralkyl groups described above. For example, it may include, but is not limited to, a methoxyl group, an ethoxyl group, a propoxyl group, a 2-ethyl-octyloxyl group and a benzyloxyl group.

The substituent the above alkyl group, aralkyl group, alkenyl group, alkynyl group and alkoxyl group may have, may include alkyl groups such as a methyl group, an ethyl group, an iso-butyl group, a sec-butyl group and a tert-butyl group; aryl groups such as a phenyl group, a terphenyl group, a naphthyl group, a biphenyl group, a fluorenyl group and a phenanthryl group; and heterocyclic groups such as a pyrrolyl group, a pyridyl group, a pyrimidyl group, a quinolyl group and a thiazolyl group.

The groups represented by $R_1$, $R_2$, $R_4$ to $R_6$ and $R_8$ to $R_{10}$ may be identical to, or different from, one another.

In the general formula (1), $R_3$ and $R_7$ each independently represent a hydrogen atom, a substituted or unsubstituted alkyl group, a substituted or unsubstituted aryl group or a substituted or unsubstituted heterocyclic group.

The alkyl group represented by $R_3$ and $R_7$ may include, but is not limited to, a methyl group, a methyl-d1 group, a methyl-d3 group, an ethyl group, an ethyl-d5 group, a n-propyl group, a n-butyl group, a n-pentyl group, a n-hexyl group, a n-heptyl group, a n-octyl group, a n-decyl group, an iso-propyl group, an iso-propyl-d7 group, an iso-butyl group, a sec-butyl group, a tert-butyl group, a tert-butyl-d9 group, an iso-pentyl group, a neopentyl group, a tert-octyl group, a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a 5-fluoropentyl group, a 6-fluorohexyl group, a chloromethyl group, a trichloromethyl group, a 2-chloroethyl group, a 2,2,2-trichloroethyl group, a 4-chlorobutyl group, a 5-chloropentyl group, a 6-chlorohexyl group, a bromomethyl group, a 2-bromoethyl group, an iodomethyl group, a 2-iodoethyl group, a hydroxymethyl group, a hydroxyethyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a norbornyl group and an adamantyl group.

The aryl group represented by $R_3$ and $R_7$ may include, but is not limited to, a phenyl group, a phenyl-d5 group, a 4-methylphenyl group, a 4-methoxylphenyl group, a 4-ethylphenyl group, a 4-fluorophenyl group, a 4-trifluorophenyl group, a 3,5-dimethylphenyl group, a 2,6-diethylphenyl group, a mesityl group, a 4-tert-butylphenyl group, a ditolylaminophenyl group, a biphenyl group, a terphenyl group, a naphthyl group, a naphthyl-d7 group, an acenaphthylenyl group, an anthryl group, an anthryl-d9 group, a phenanthryl group, a phenanthryl-d9 group, a pyrenyl group, a pyrenyl-d9 group, an acephenanthrenyl group, an aceanthrenyl group, an chrysenyl group, a dibenzochrysenyl group, a benzoanthryl group, a benzoanthryl-d11 group, a dibenzoanthryl group, a naphthacenyl group, a picenyl group, a pentacenyl group, a fluorenyl group, a triphenylenyl group, a perylenyl group and a perylenyl-d11 group.

The heterocyclic group represented by $R_3$ and $R_7$ may include, but is not limited to, a pyrrolyl group, a pyridyl group, a pyridyl-d5 group, a bipyridyl group, a methylpyridyl group, a pyrimidinyl group, a pyrazinyl group, a pyridazinyl group, a terpyrrolyl group, a thienyl group, a thienyl-d4 group, a terthienyl group, a propylthienyl group, a benzothienyl group, a dibenzothienyl group, a dibenzothienyl-d7 group, a furyl group, a furyl-d4 group, a benzofuryl group, an isobenzofuryl group, a dibenzofuryl group, a dibenzofuryl-d7 group, a quinolyl group, a quinolyl-d6 group, an isoquinolyl group, a quinoxalinyl group, a naphthylidinyl group, a quinazolinyl group, a phenanethridinyl group, an indolidinyl group, a phenazinyl group, a carbazolyl group, an oxazolyl group, an oxadiazolyl group, a thiazolyl group, a thiadiazolyl group, an acridinyl group and a phenazinyl group.

The substituent the above alkyl group, aryl group and heterocyclic group may have, may include, but is not limited to, alkyl groups such as a methyl group, an ethyl group, a tert-butyl group, an iso-butyl group and a sec-butyl group; alkoxyl groups such as a methoxyl group and an ethoxyl; aryl groups such as a phenyl group, a terphenyl group, a naphthyl group, a biphenyl group, a fluorenyl group and a phenanthryl group; and heterocyclic groups such as a pyrrolyl group, a pyridyl group, a pyrimidyl group, a quinolyl group and a thiazolyl group.

The groups represented by $R_3$ and $R_7$ may be identical to, or different from, each other.

In the general formula (1), $X_1$ and $X_2$ each represent —$CR_{11}R_{12}$— or —$NR_{11}$—.

Here, $R_{11}$ and $R_{12}$ each independently represent a hydrogen atom, an alkyl group, a substituted or unsubstituted aralkyl group, a substituted or unsubstituted aryl group, a substituted or unsubstituted heterocyclic group or a halogen atom.

The alkyl group represented by $R_{11}$ and $R_{12}$ may include, but is not limited to, a methyl group, a methyl-d1 group, a methyl-d3 group, an ethyl group, an ethyl-d5 group, a n-propyl group, a n-butyl group, a n-pentyl group, a n-hexyl group, a n-heptyl group, a n-octyl group, a n-decyl group, an iso-propyl group, an iso-propyl-d7 group, an iso-butyl group, a sec-butyl group, a tert-butyl group, a tert-butyl-d9 group, an iso-pentyl group, a neopentyl group, a tert-octyl group, a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a 5-fluoropentyl group, a 6-fluorohexyl group, a chloromethyl group, a trichloromethyl group, a 2-chloroethyl group, a 2,2,2-trichloroethyl group, a 4-chlorobutyl group, a 5-chloropentyl group, a 6-chlorohexyl group, a bromomethyl group, a 2-bromoethyl group, an iodomethyl group, a 2-iodoethyl group, a hydroxymethyl group, a hydroxyethyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a norbornyl group and an adamantyl group.

The aralkyl group represented by $R_{11}$ and $R_{12}$ may include, but is not limited to, a benzyl group, a 2-phenylethyl group, a 2-phenylisopropyl group, a 1-naphtylmethyl group, a 2-naphtylmethyl group, a 2-(1-naphthyl)ethyl group, a 2-(2-naphthyl)ethyl group, a 9-anthrylmethyl group, a 2-(9-anthryl)ethyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group and a 4-bromobenzyl group.

The aryl group represented by $R_{11}$ and $R_{12}$ may include, but is not limited to, a phenyl group, a phenyl-d5 group, a 4-methylphenyl group, a 4-methoxylphenyl group, a 4-ethylphenyl group, a 4-fluorophenyl group, a 4-trifluorophenyl group, a 3,5-dimethylphenyl group, a 2,6-diethylphenyl group, a mesityl group, a 4-tert-butylphenyl group, a ditolylaminophenyl group, a biphenyl group, a terphenyl group, a naphthyl group, a naphthyl-d7 group, an acenaphthylenyl group, an anthryl group, an anthryl-d9 group, a phenanthryl group, a phenanthryl-d9 group, a pyrenyl group, a pyrenyl-d9 group, an acephenanthrenyl group, an aceanthrenyl group, an chrysenyl group, a dibenzochrysenyl group, a benzoanthryl group, a benzoanthryl-d11 group, a dibenzoanthryl group, a naphthacenyl group, a picenyl group, a pentacenyl group, a fluorenyl group, a triphenylenyl group, a perylenyl group and a perylenyl-d11 group.

The heterocyclic group represented by $R_{11}$ and $R_{12}$ may include, but is not limited to, a pyrrolyl group, a pyridyl group, a pyridyl-d5 group, a bipyridyl group, a methylpyridyl group, a pyrimidinyl group, a pyrazinyl group, a pyridazinyl group, a terpyrrolyl group, a thienyl group, a thienyl-d4 group, a terthienyl group, a propylthienyl group, a benzothienyl group, a dibenzothienyl group, a dibenzothienyl-d7 group, a furyl group, a furyl-d4 group, a benzofuryl group, an isobenzofuryl group, a dibenzofuryl group, a dibenzofuryl-d7 group, a quinolyl group, a quinolyl-d6 group, an isoquinolyl group, a quinoxalinyl group, a naphthyridinyl group, a quinazolinyl group, a phenanethridinyl group, an indolidinyl group, a phenazinyl group, a carbazolyl group, an oxazolyl group, an oxadiazolyl group, a thiazolyl group, a thiadiazolyl group, an acridinyl group and a phenazinyl group.

The halogen atom represented by $R_{11}$ and $R_{12}$ may include, but is not limited to, a fluorine atom, a chlorine atom, a bromine atom and an iodine atom.

The substituent the above aralkyl group, aryl group and heterocyclic group may have, may include, but is not limited to, alkyl groups such as a methyl group, an ethyl group, an iso-butyl group, a sec-butyl group and a tert-butyl group; aryl groups such as a phenyl group, a terphenyl group, a naphthyl group, a biphenyl group, a fluorenyl group and a phenanthryl group; and heterocyclic groups such as a pyrrolyl group, a pyridyl group, a pyrimidyl group, a quinolyl group and a thiazolyl group.

The groups represented by $R_{11}$ and $R_{12}$ may be identical to, or different from, each other. The groups represented by $X_1$ and $X_2$ may be identical to, or different from, each other.

The biphenyl derivative of the present invention is the compound represented by the general formula (1), and is a compound usable as a material for organic light-emitting elements. It has such structural features as shown below.

(1) The biphenyl skeleton is substituted at least at the 3- and 5'-positions with groups selected from a fluorenyl group and a carbazolyl group.

(2) The biphenyl skeleton is substituted with two or more groups selected from a fluorenyl group and a carbazolyl group.

In order to improve the luminous efficiency of the organic light-emitting element, excitons produced in its light-emitting layer must be confined in the light-emitting layer. Here, in the case of an organic light-emitting element having a phosphorescent compound as the guest of the light-emitting layer, the corresponding host must have an energy level ($S_1$) in a minimum excitation singlet excitation state and an energy level ($T_1$) in a triplet excitation state which are higher than the energy level of the guest.

For example, where a phosphorescent compound which emits light in the range of from green to blue (light emission peak: 480 nm to 520 nm) is used as the guest of the light-emitting layer, it is desirable for the corresponding host to have a $T_1$ of 500 nm or less in terms of the wavelength of light.

The $T_1$ of biphenyl and of a compound whose biphenyl skeleton is substituted with an aryl group such as phenyl will be described here. According to the above Non-patent Document 3, the $T_1$ of biphenyl (Compound P2) and of 1,1':4'1''-terphenyl (Compound P3) in which biphenyl is substituted with one phenyl group at the 4 (or 4')-position, are as shown below.

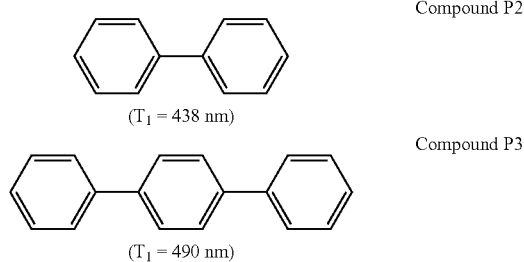

Compound P2
($T_1$ = 438 nm)

Compound P3
($T_1$ = 490 nm)

Hence, if a phenyl group is further linked to Compound P3 at the 4 (or 4'')-position, the $T_1$ comes to be more than 500 nm in terms of the wavelength of light. Accordingly, such a compound in which an aryl group such as phenyl is introduced into biphenyl at each of the 4- and 4'-positions is not suitable as the host corresponding to the phosphorescent compound (guest) which emits light in the range of from green to blue.

The reason therefor is considered to be that the conjugation length of the molecule itself extends because of the introduction of the aryl groups such as phenyl groups respectively at the 4- and 4'-positions of the biphenyl. Such extension of the conjugation length of the molecule itself makes it difficult to keep the $T_1$ high. The conjugation length of the molecule itself extends also in a case where an aryl group such as phenyl is introduced into biphenyl at each of the 2 (or 6)-position and 2'(or 6')-position of the biphenyl, and hence this makes it difficult to keep the $T_1$ high.

On the other hand, when an aryl group such as phenyl is introduced into the biphenyl skeleton as in the biphenyl derivative of the present invention at each of the 3- and 5'-positions, the conjugation does not extend. Thus, when the aryl groups advantageous to transport of electric charges are introduced into the biphenyl skeleton at the 3- and 5'-positions, the conjugation length of the molecule itself can be controlled.

Thus, it is possible to keep the $T_1$ and $S_1$ high by introducing the aryl groups such as phenyl groups respectively at the 3- and 5'-positions of the biphenyl skeleton.

When an aryl group such as phenyl is introduced into the biphenyl skeleton at each of the 3 (or 5)-position and 5' (or 3')-position, however, the steric hindrance of the aryl group is small as long as it is introduced at these positions, and hence the substituent itself can easily rotate. Thus, the rigidity of the molecule itself is reduced, and the glass transition point (Tg) and melting point (Tm) of the compound are lowered. If a material contained in an organic light-emitting element has a low Tg, the thermal stability of the organic light-emitting element is lowered, which is disadvantageous to the application to displays or the like.

In the biphenyl derivative of the present invention, the aryl group introduced into the biphenyl skeleton at each of the 3- and 5'-positions is a fluorenyl group or a carbazolyl group. The introduction of a fluorenyl group and/or a carbazolyl group makes the thermal stability of the organic light-emitting element superior, while keeping the high $T_1$ and $S_1$ of the host.

In general, a certain degree of molecular weight is required in order to make the Tg and Tm higher. However, in order to make the Tg and Tm higher while keeping the $T_1$ and $S_1$ high, it is preferable that the fluorenyl group and/or carbazolyl group are/is introduced into the biphenyl skeleton at the 3-position, 5-position, 3'-position and 5'-position. It is also preferable that a substituent which does not extend the conjugation length of the molecule, such as alkyl groups, is introduced into each of the fluorenyl group and carbazolyl group at the 7-position.

A substituent is introduced into each of the fluorenyl group and carbazolyl group at the 9-position, where an alkyl group is preferred as the substituent. The alkyl group to be introduced into each of the fluorenyl group and carbazolyl group at the 9-position may have a long chain length, but is preferably a methyl group, taking the glass transition point and melting point into account. However, an alkyl group having a longer chain than a methyl group, such as an ethyl group, a propyl group or a butyl group, may be introduced. From the viewpoint of synthesis, the alkyl groups introduced respectively into the fluorenyl group and carbazolyl group at the 9-positions are preferably identical. However, the alkyl groups introduced at the 9-positions may be different from each other.

When the light-emitting layer is composed of a host and a guest, the guest and the host play roles of light emission and charge transport, respectively. Hence, such charge transport performance of the host plays an important role in the light-emitting layer. On the other hand, in the charge transport layer as well, the charge transport performance for transporting electric charges to the light-emitting layer plays an important role. If the charge transport layer has low charge transport performance, the drive voltage of the organic light-emitting element will increase, and its lifetime is shortened. Consequently, it is desirable for the host or charge transport layer to have higher charge transport performance.

Accordingly, for the purpose of making the charge transport performance higher, in the biphenyl derivative of the present invention, at least two groups selected from a fluorenyl group and a carbazolyl group are introduced into the biphenyl skeleton which is the central skeleton of the biphenyl derivative. In addition, in the biphenyl derivative of the present invention, the fluorenyl group and carbazolyl group to be introduced are coupled at their 2-positions. Thus, the linearity of the molecule itself increases so that charge transport performance is expected to increase.

In the following, examples of the biphenyl derivative of the present invention are shown by specific structural formulas. However, they are only typical examples to which the present invention is by no means limited.
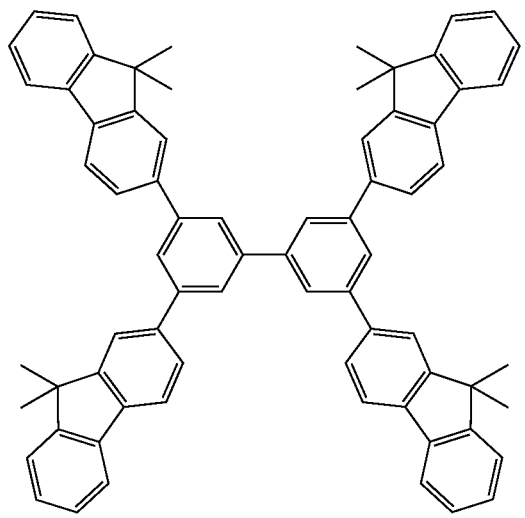
H-1
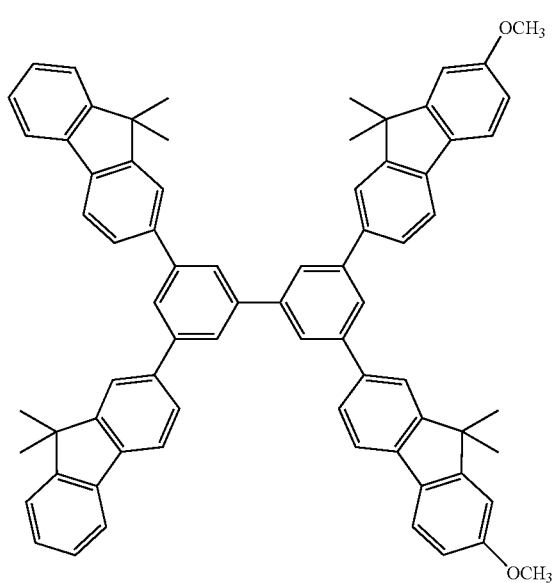
H-2
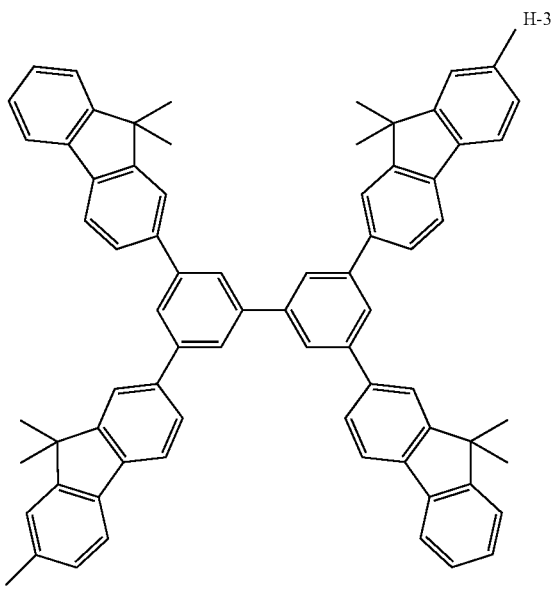
H-3
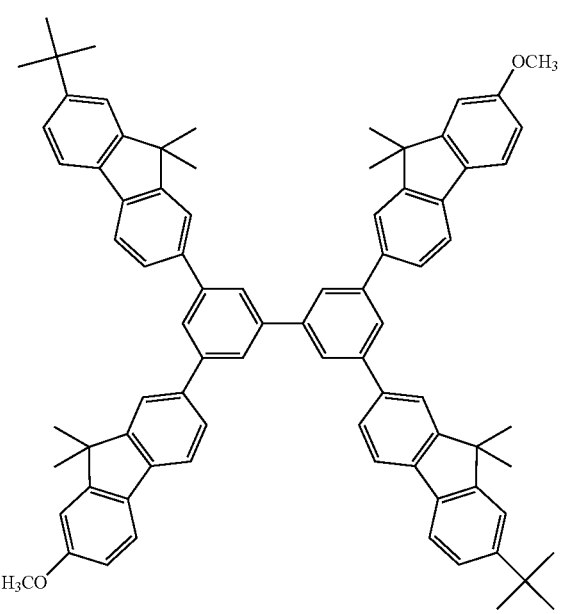
H-4

H-5
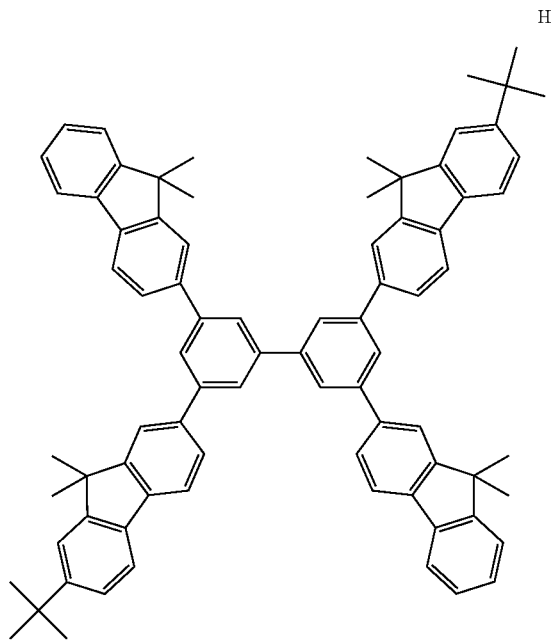
H-7
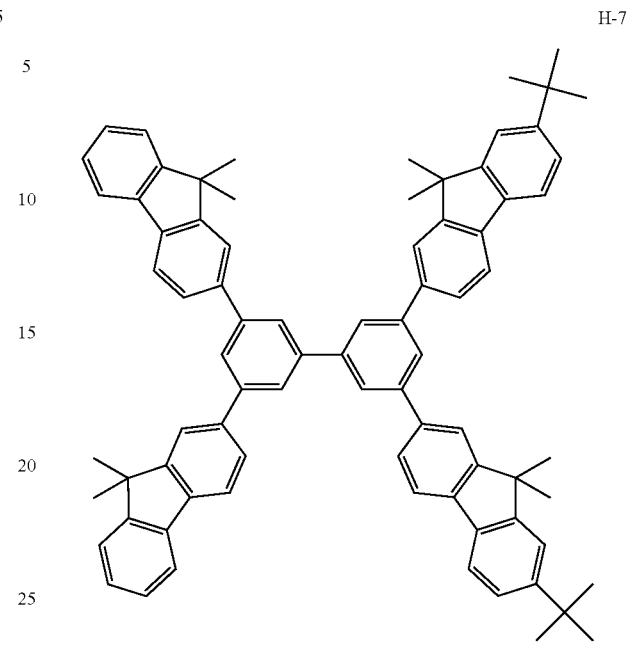
H-6
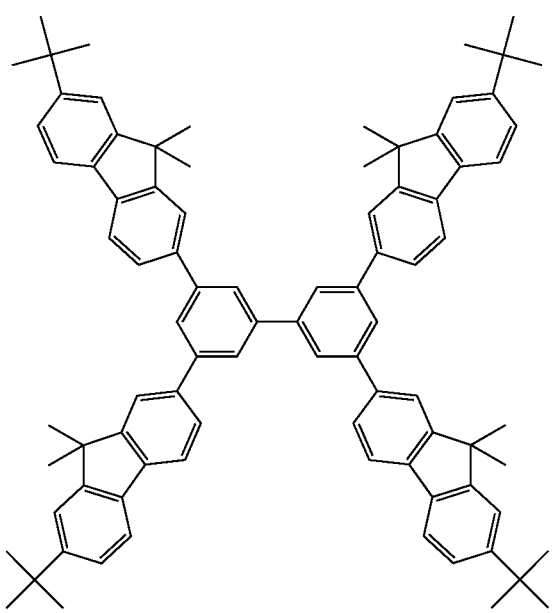
H-8
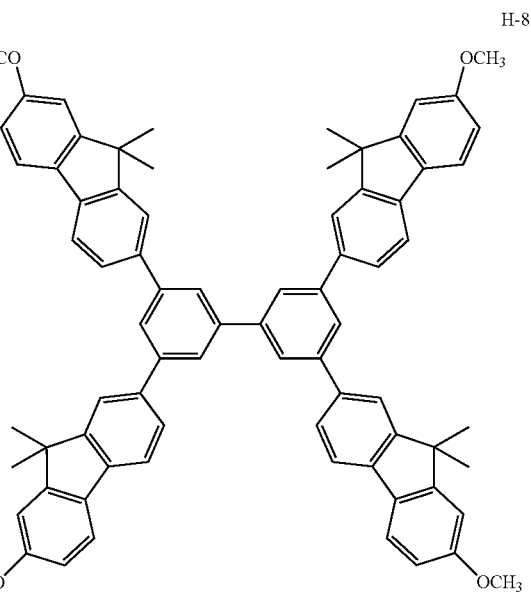

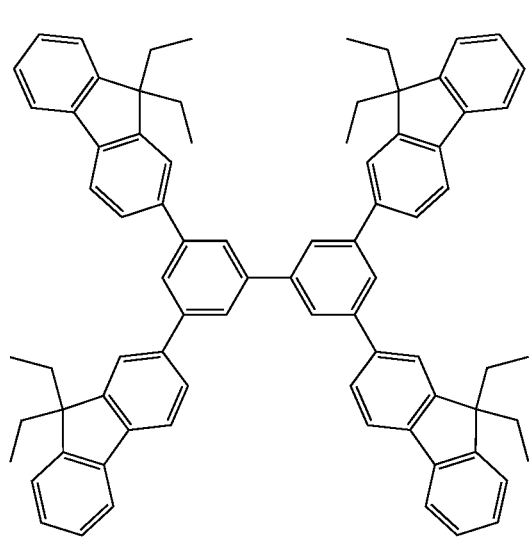
H-9
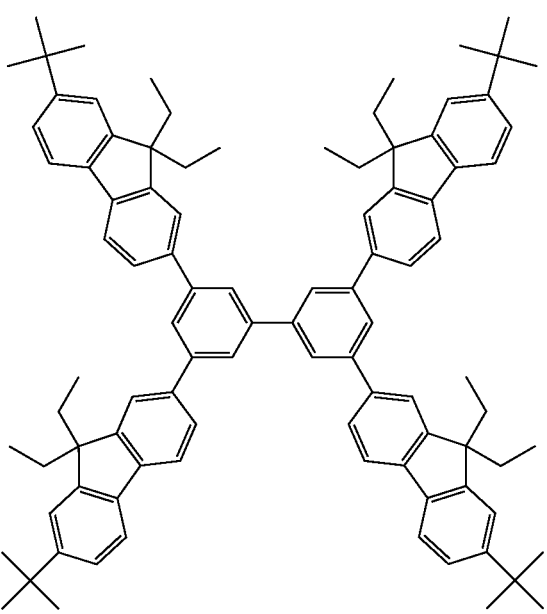
H-11
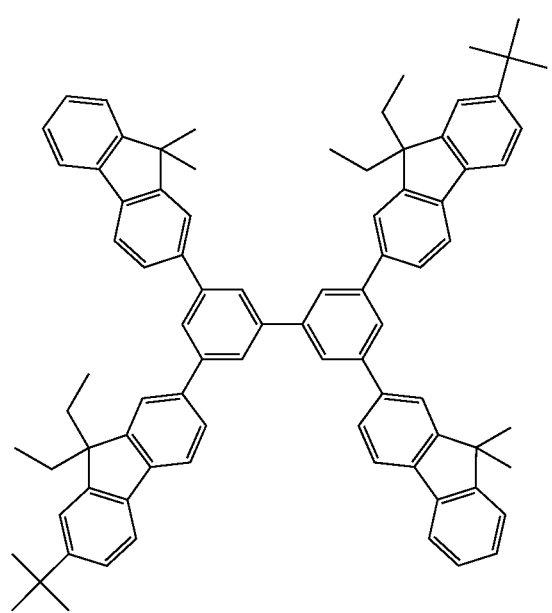
H-10
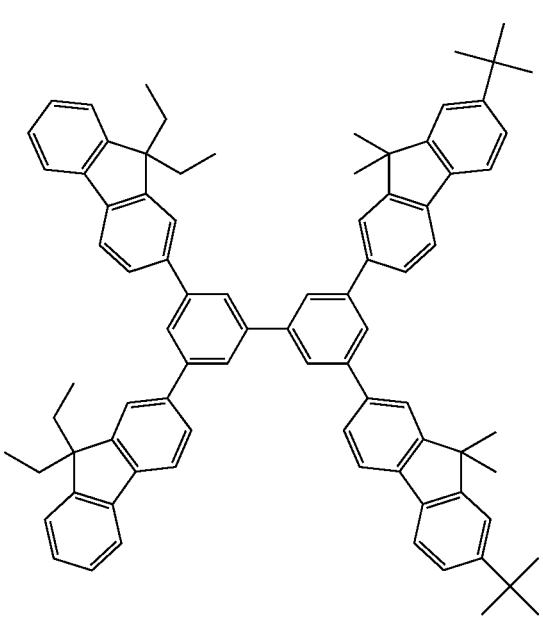
H-12

-continued
H-13
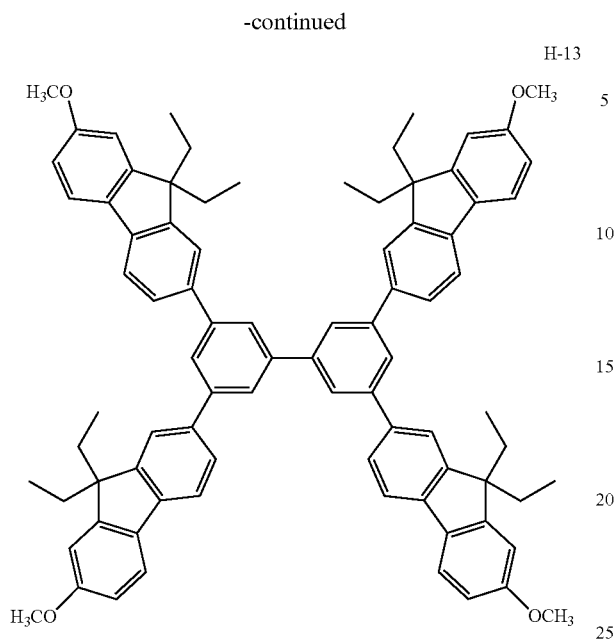
H-15
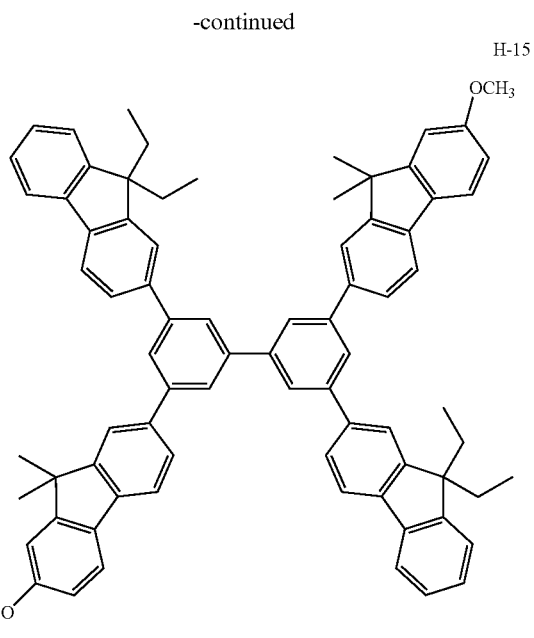
H-14
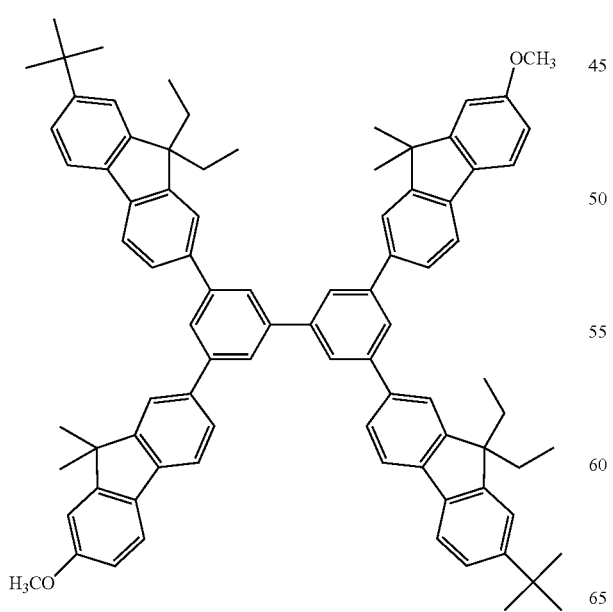
H-16
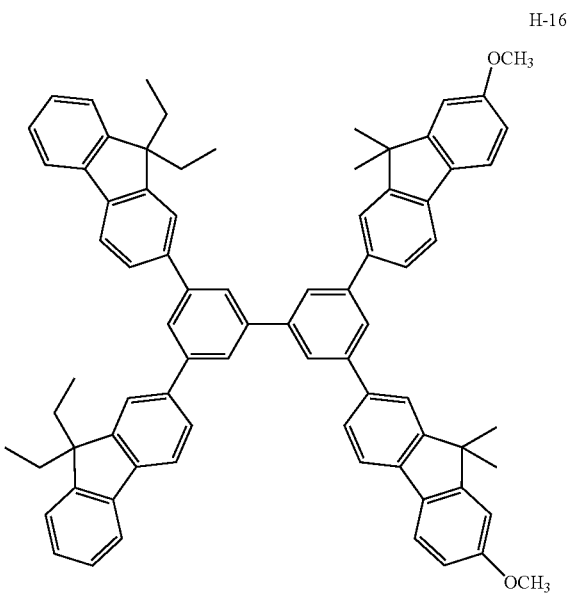

-continued
H-17
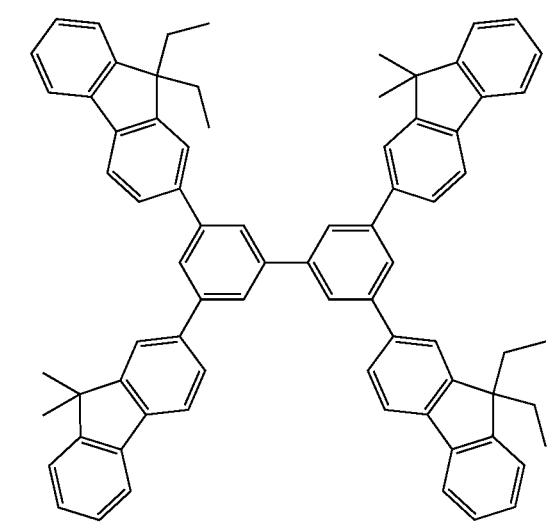
H-18
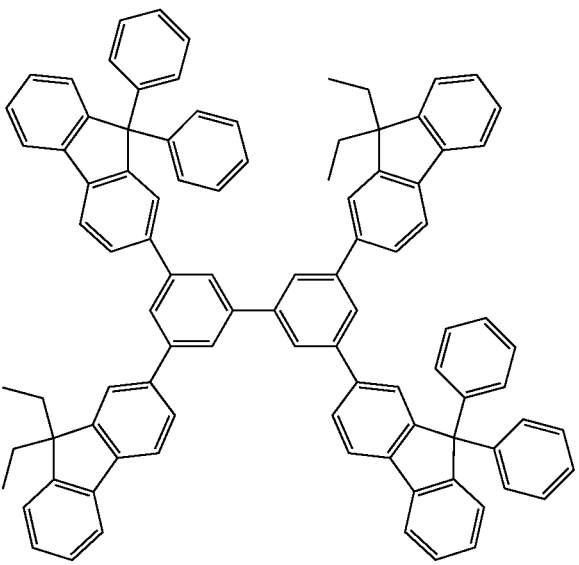
H-19
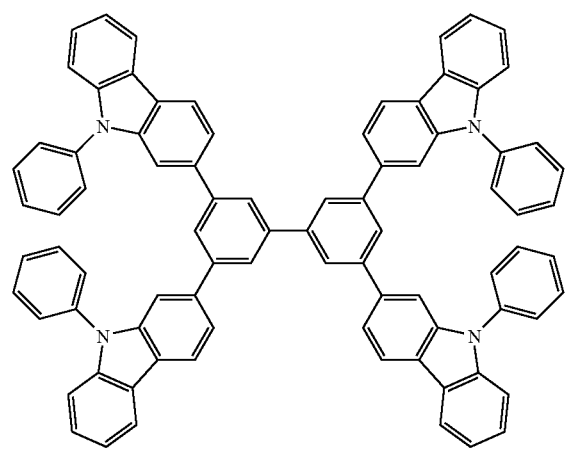
-continued
H-20
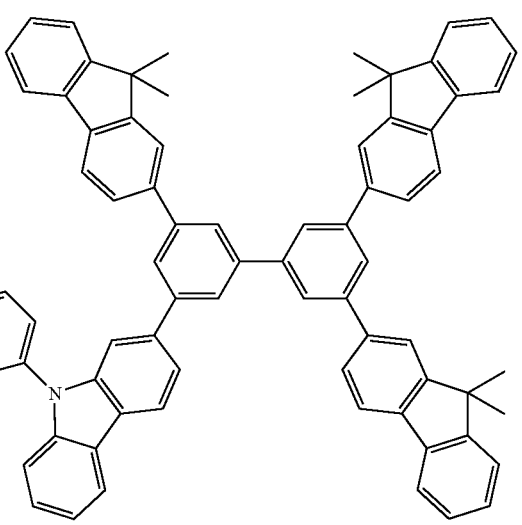
H-21
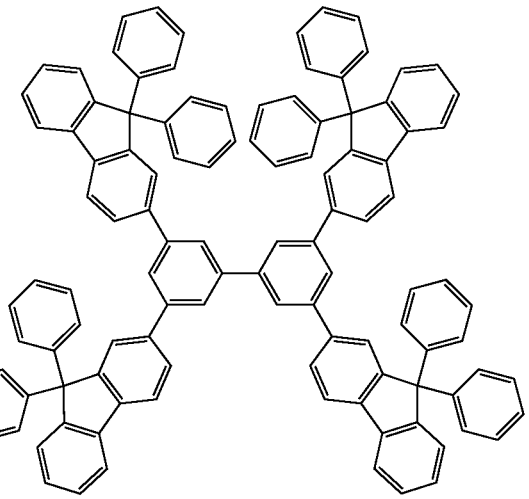
H-22
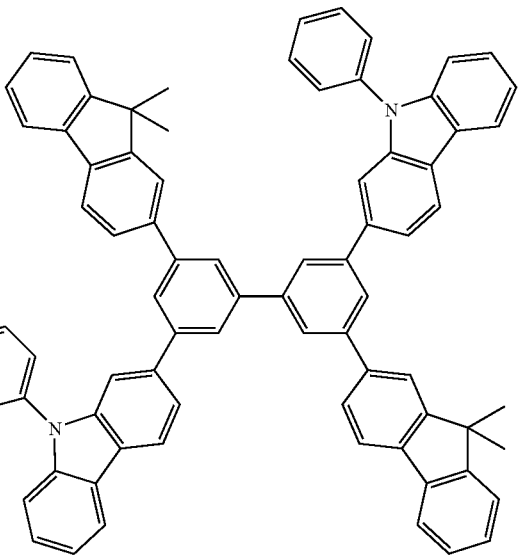

-continued
H-23
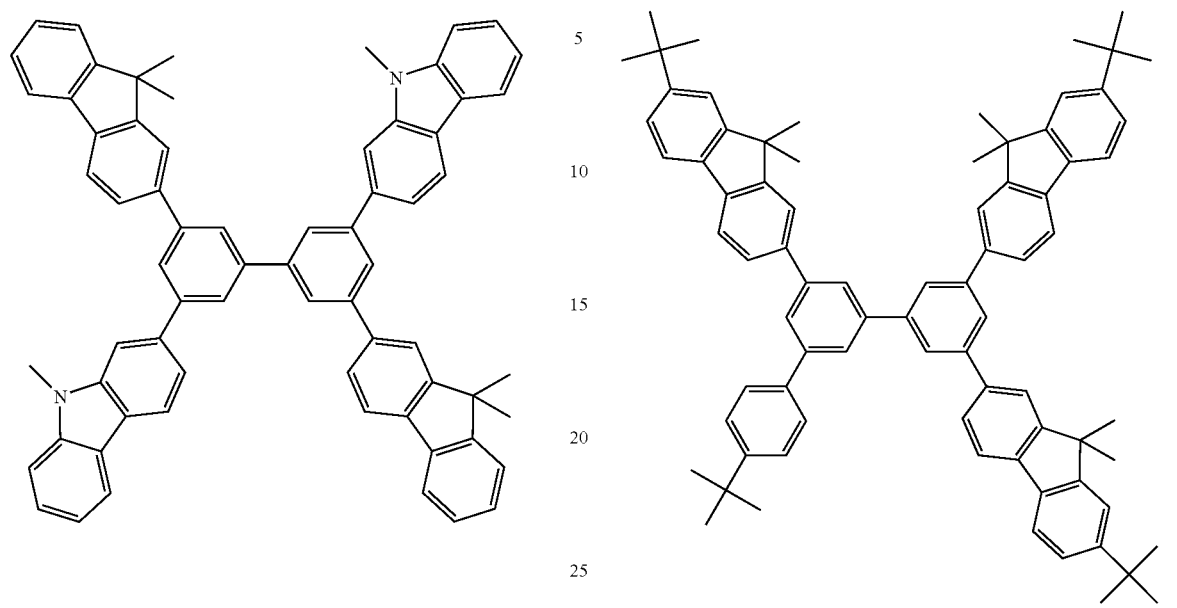
H-24
H-25
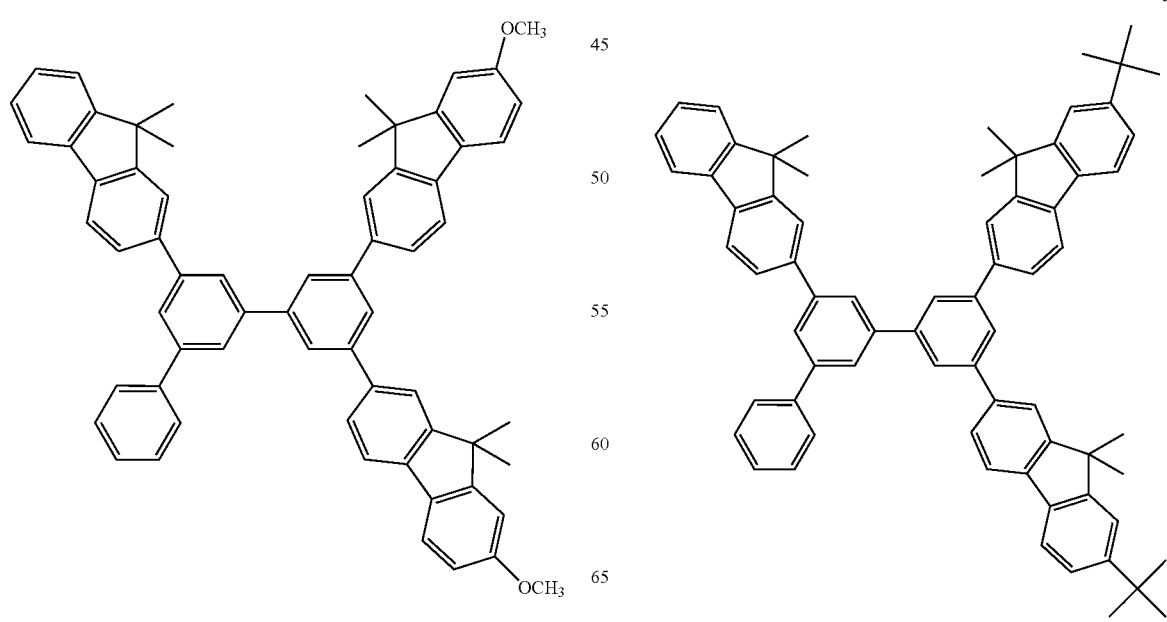
H-26

H-27
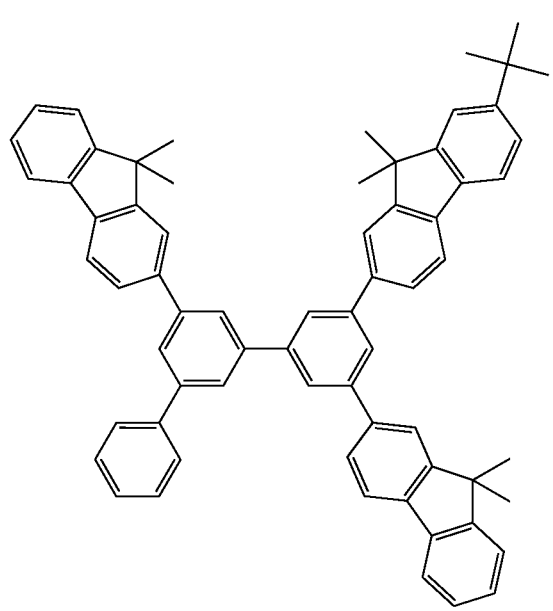
H-29
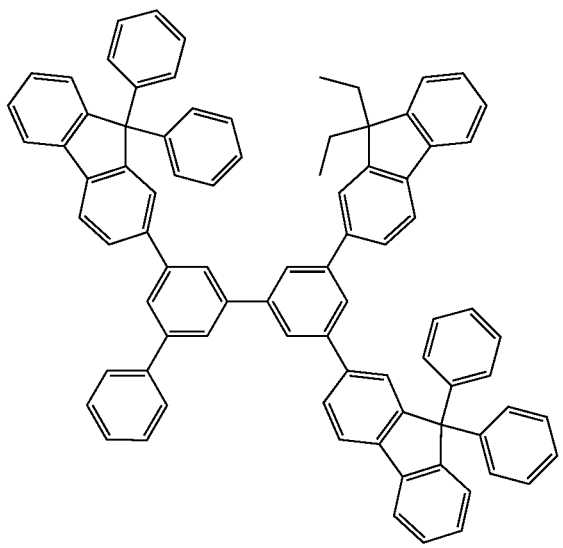
H-28
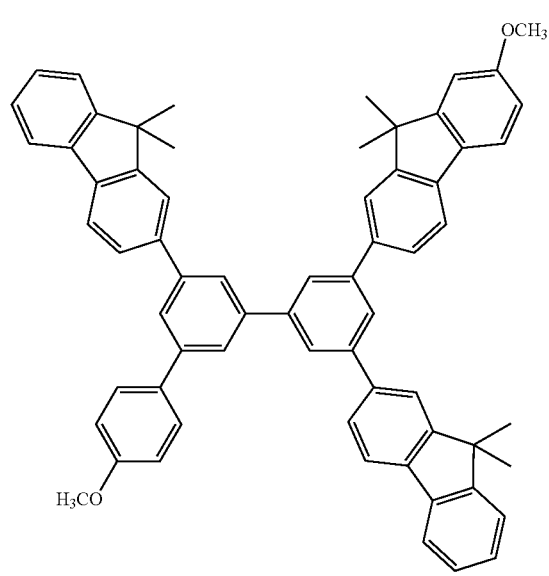
H-30
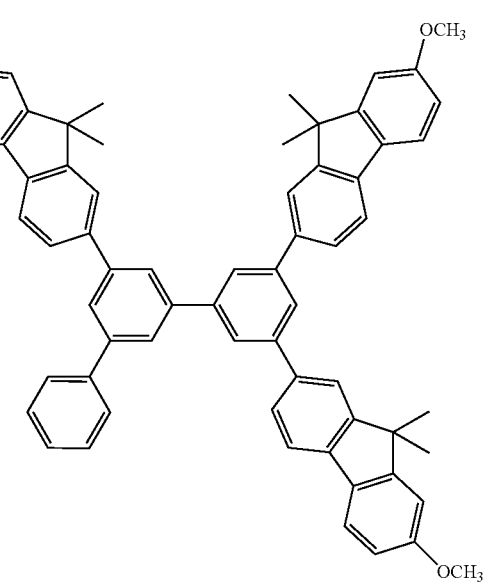

H-31
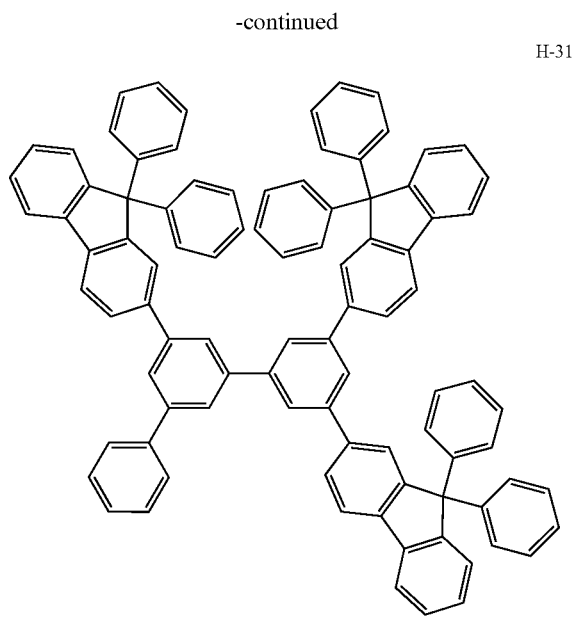
H-32
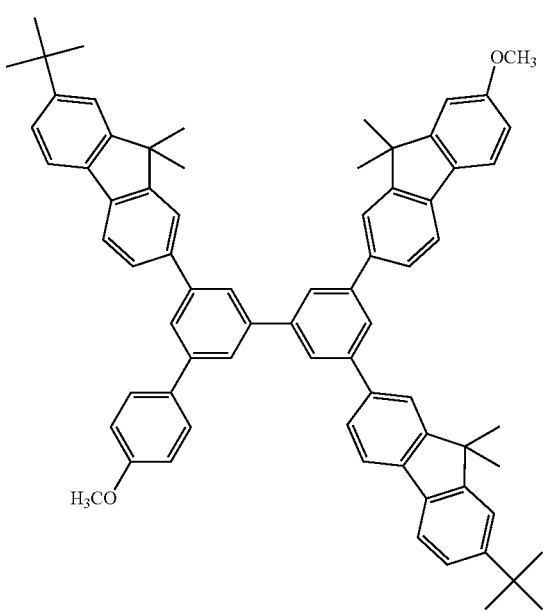
H-33
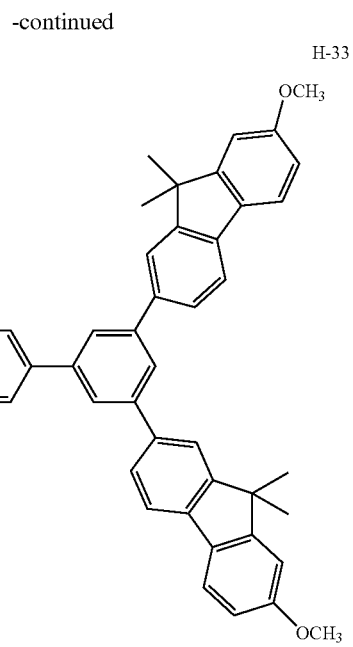
H-34
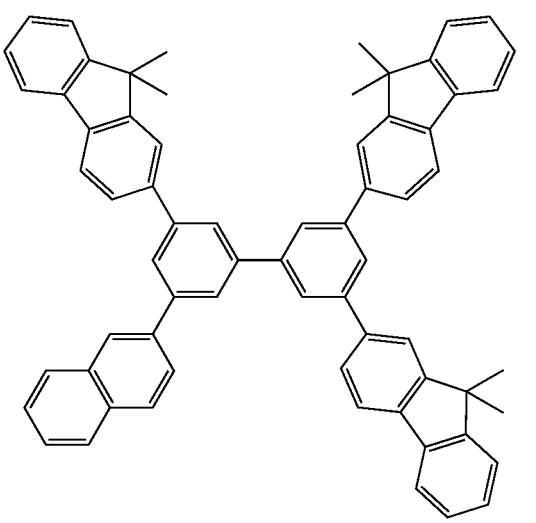

-continued
H-35
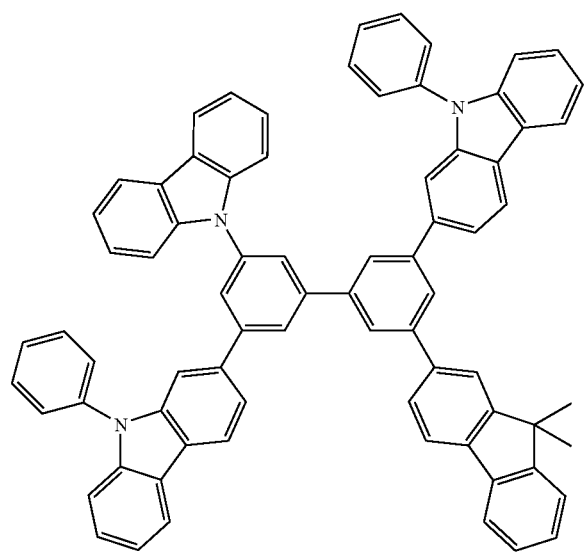
H-36
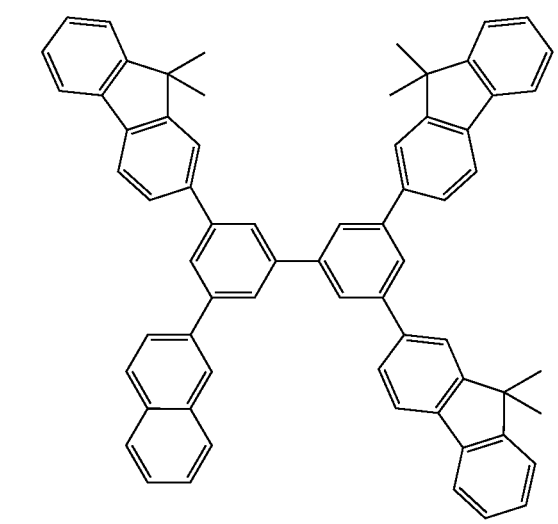
H-37
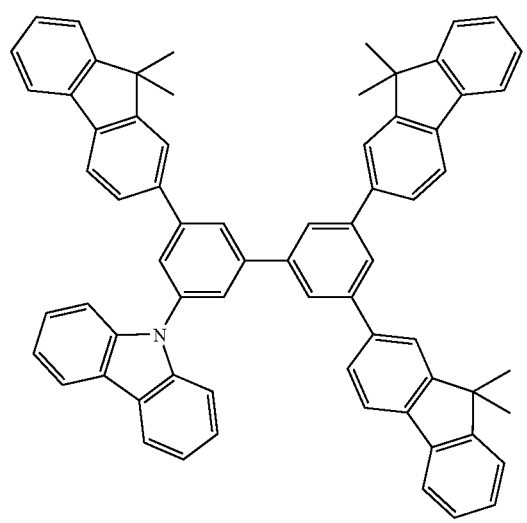
-continued
H-38
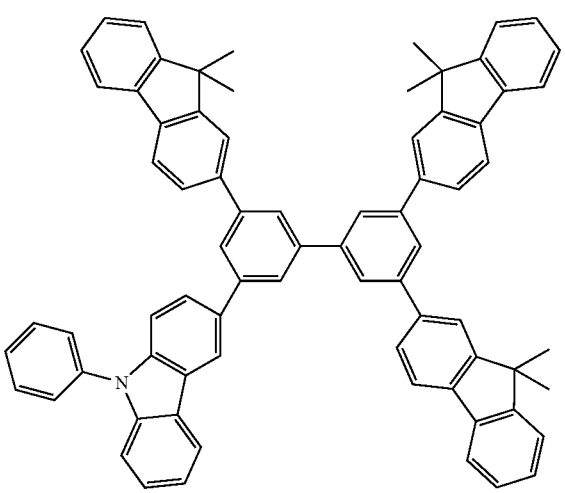
H-39
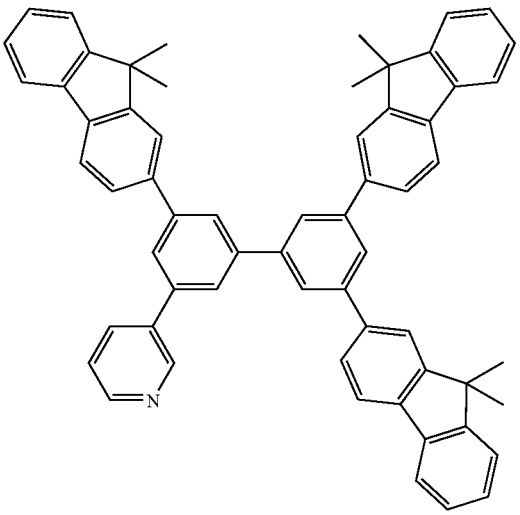
H-40
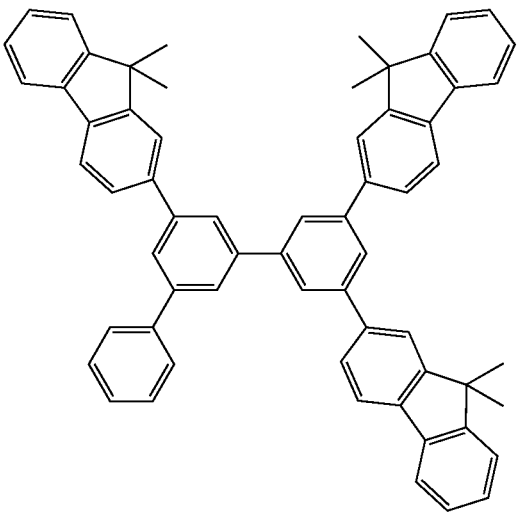

H-41
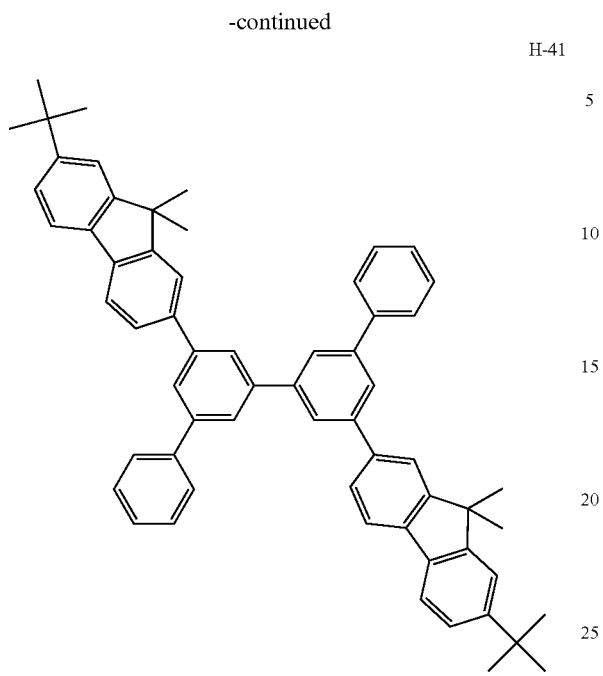
H-43
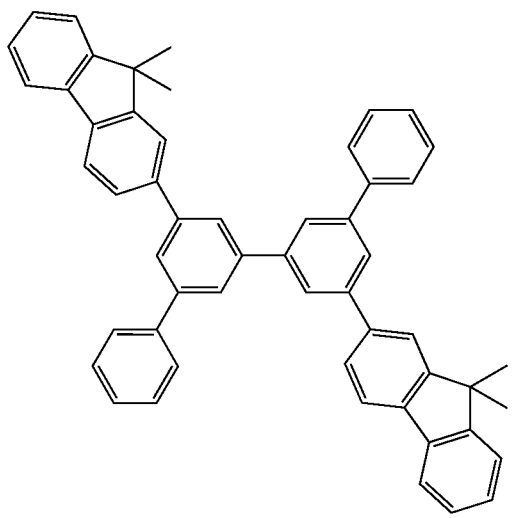
H-42
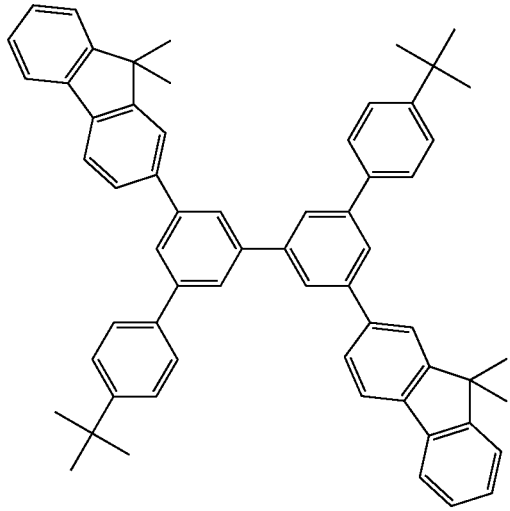
H-44
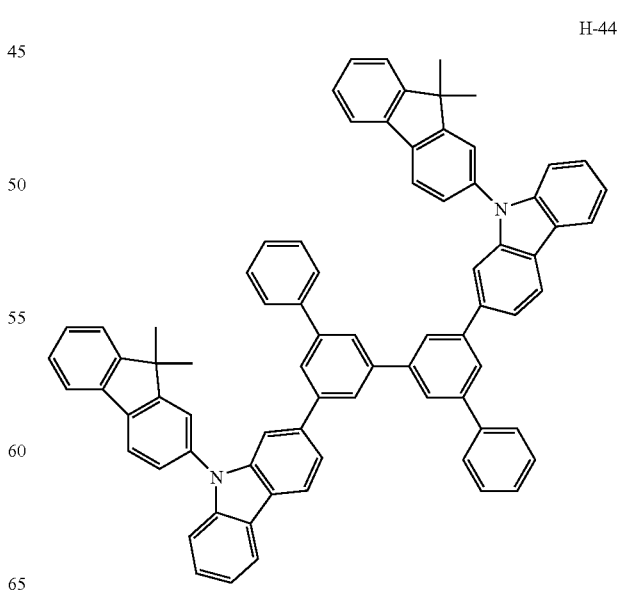

H-45
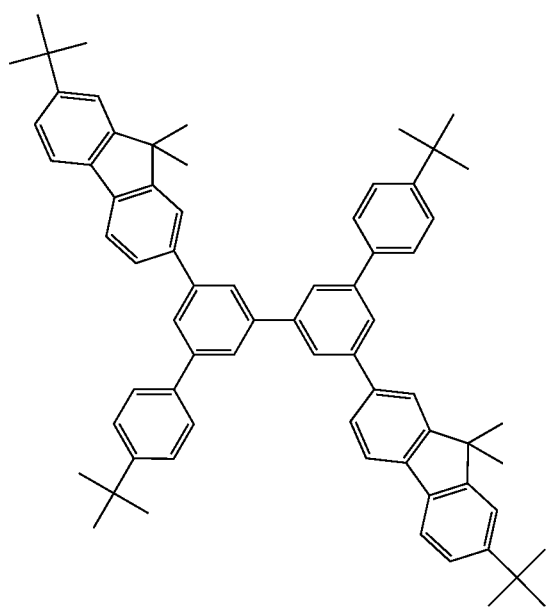
H-47
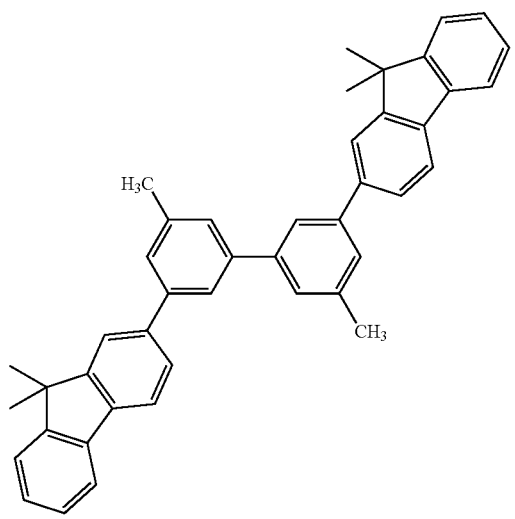
H-46
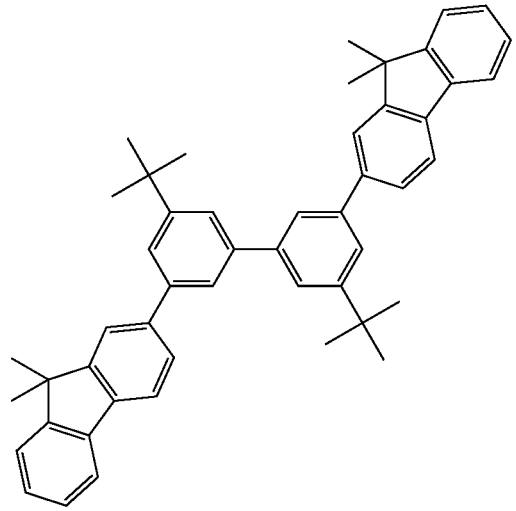
H-48
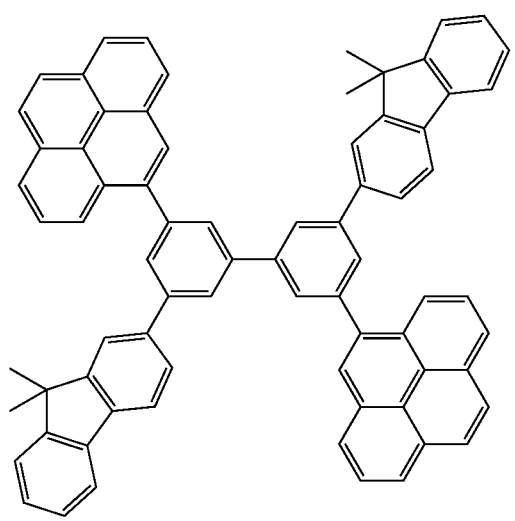

-continued
H-49
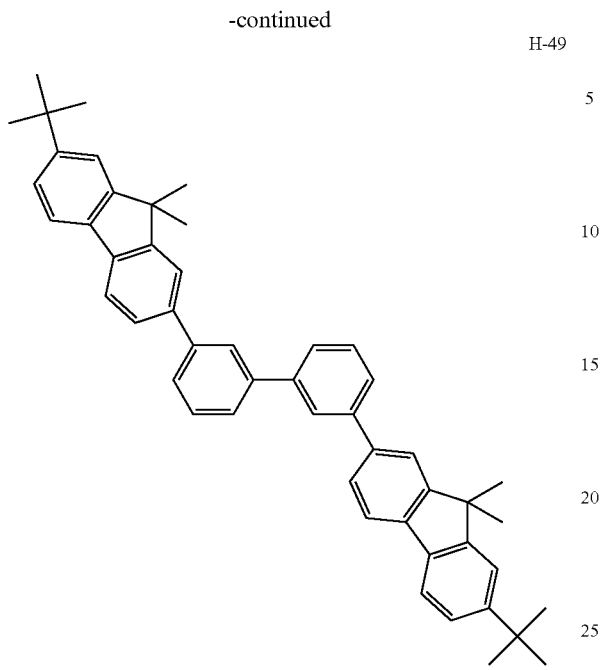
H-51
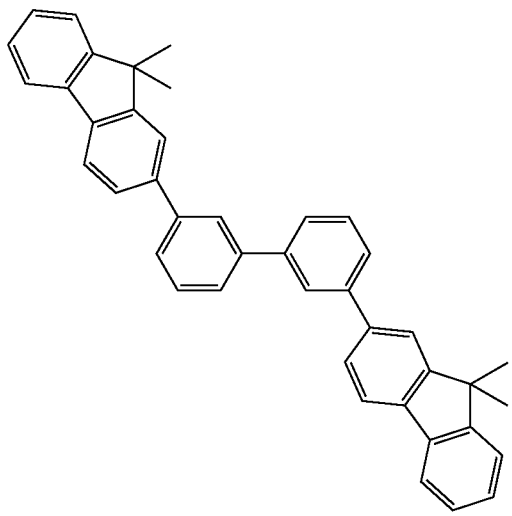
H-50
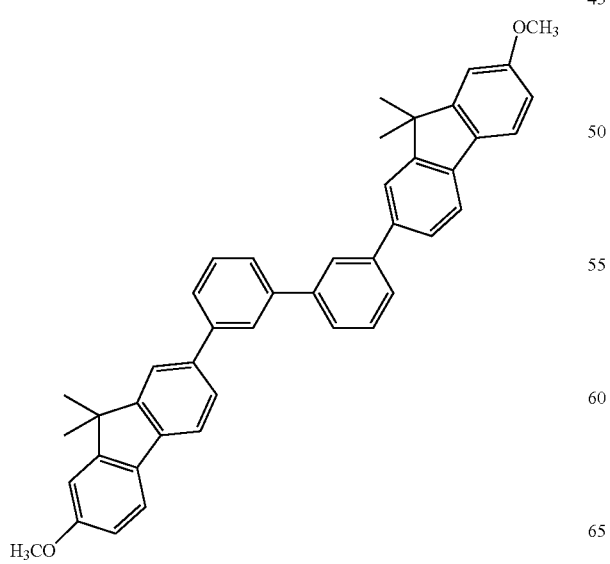
H-52
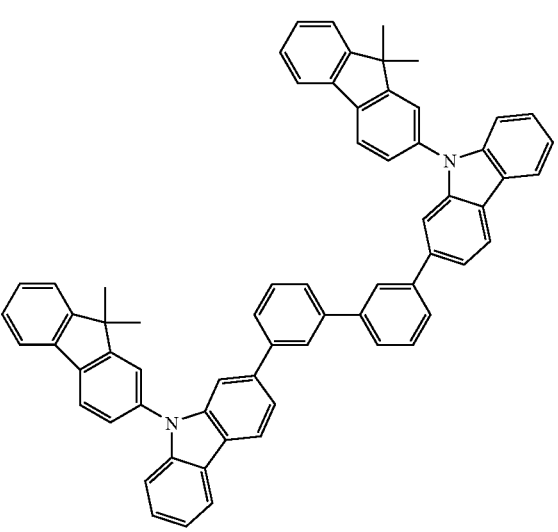

-continued

H-53
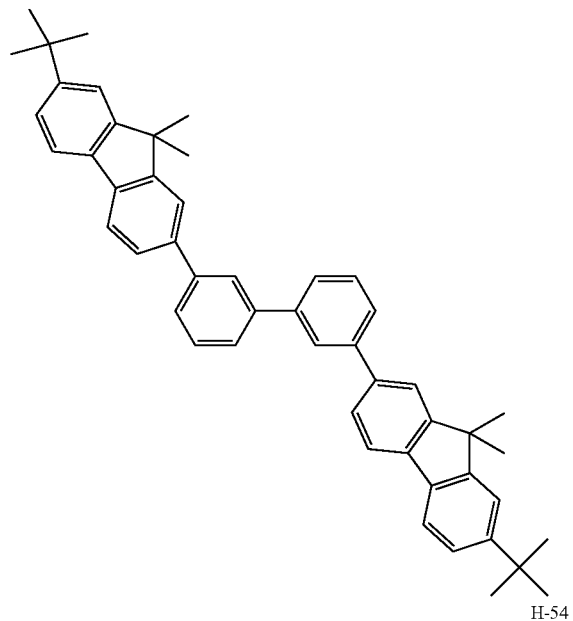

H-54
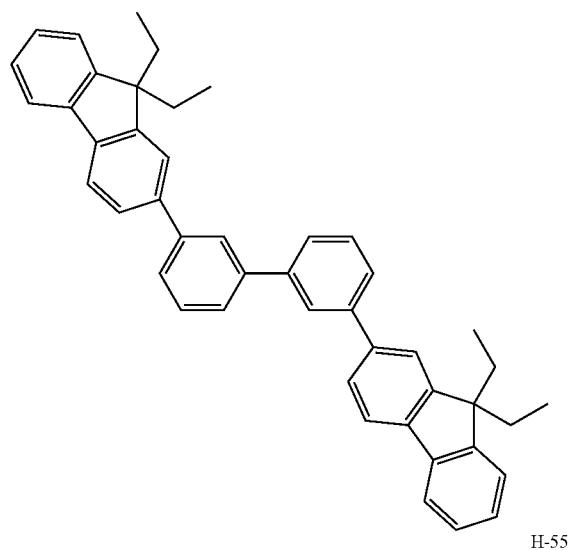

H-55
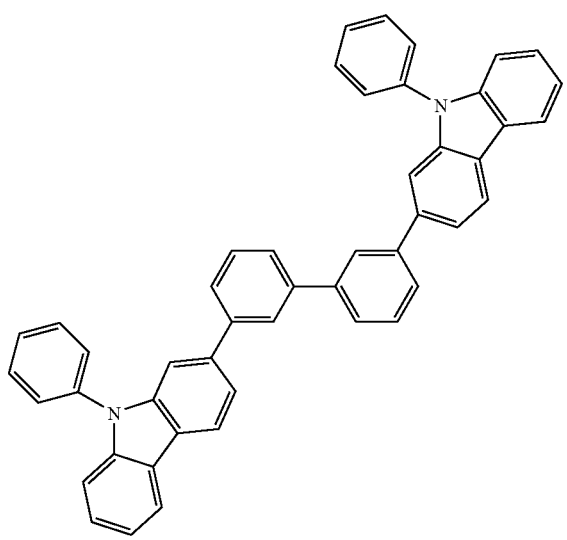

The organic light-emitting element of the present invention is described next in detail.

The organic light-emitting element of the present invention consists basically of an anode and a cathode, and a layer which contains an organic compound and is held between the anode and the cathode. In the organic light-emitting element of the present invention, the layer containing an organic compound contains at least one biphenyl derivative of the present invention.

The organic light-emitting element of the present invention is described below in detail with reference to the drawings.

It is first described what reference numerals shown in the drawings denote.

Reference numeral 1 denote a substrate; 2, an anode; 3, a light-emitting layer; 4, a cathode; 5, a hole transport layer; 6, an electron transport layer; 7, a hole injection layer; 8, a hole/exciton blocking layer; and 9, a electron injection layer. Reference numerals 10, 20, 30, 40, 50 and 60 each denote an organic light-emitting element.

FIG. 1 is a sectional view showing a first embodiment of the organic light-emitting element of the present invention. The organic light-emitting element 10 as shown in FIG. 1 has the substrate 1, and the anode 2, the light-emitting layer 3 and the cathode 4 in this order formed on the support. This organic light-emitting element 10 is useful when the light-emitting layer 3 is made up of an organic compound having all of hole transport performance, electron transport performance and a luminescent property. This organic light-emitting element is also useful when the light-emitting layer 3 is made up of a mixture of compounds having respectively hole transport performance, electron transport performance and a luminescent property.

Figure 2:
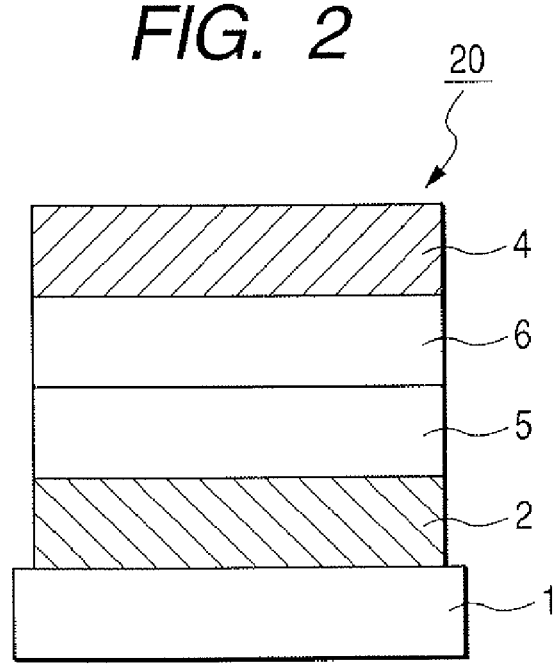
FIG. 2 is a sectional view showing a second embodiment in the organic light-emitting element of the present invention.

FIG. 2 is a sectional view showing a second embodiment of the organic light-emitting element of the present invention. The organic light-emitting element 20 as shown in FIG. 2 has the substrate 1, and the anode 2, the hole transport layer 5, the electron transport layer 6 and the cathode 4 in this order formed on the support. This organic light-emitting element 20 is useful when a luminescent organic compound having either hole transport performance or electron transport performance and an organic compound having electron transport performance only or hole transport performance only are used in combination. In the organic light-emitting element 20, the hole transport layer 5 or the electron transport layer 6 serves also as a light-emitting layer.

Figure 3:
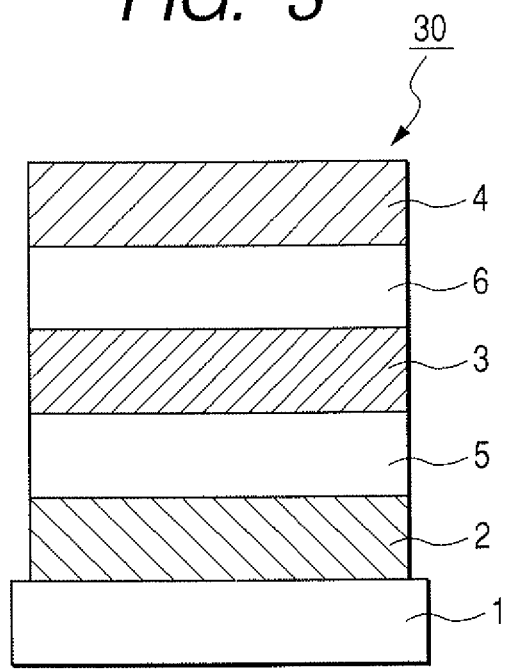
FIG. 3 is a sectional view showing a third embodiment in the organic light-emitting element of the present invention.

FIG. 3 is a sectional view showing a third embodiment of the organic light-emitting element of the present invention. The organic light-emitting element 30 as shown in FIG. 3 is one in which, in the organic light-emitting element 20 as shown in FIG. 2, the light-emitting layer 3 is inserted between the hole transport layer 5 and the electron transport layer 6. This organic light-emitting element 30 is one in which functions of carrier transport and light emission are separated, where organic compounds having respectively hole transport performance, electron transport performance and a luminescent property are used in appropriate combination. Hence, materials can be selected with a very large degree of freedom and various organic compounds emitting light different in wavelength can be used, and hence light with various hues can be emitted. Further, carriers or excitons can effectively be confined in the light-emitting layer 3 at the center to achieve an improvement in luminous efficiency.

Figure 4:
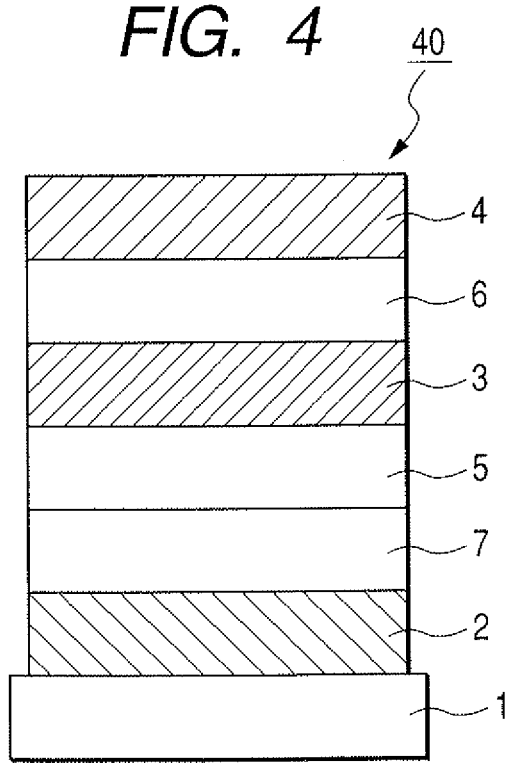
FIG. 4 is a sectional view showing a fourth embodiment in the organic light-emitting element of the present invention.

FIG. 4 is a sectional view showing a fourth embodiment of the organic light-emitting element of the present invention. The organic light-emitting element 40 as shown in FIG. 4 is one in which, in the organic light-emitting element 30 as shown in FIG. 3, the hole injection layer 7 is inserted between the anode 2 and the hole transport layer 5. This organic light-emitting element 40 is improved in the adhesion between the anode 2 and the hole transport layer 5 or the hole injection performance because the hole injection layer 7 is provided, and hence, this is effective in reducing voltage.

Figure 5:
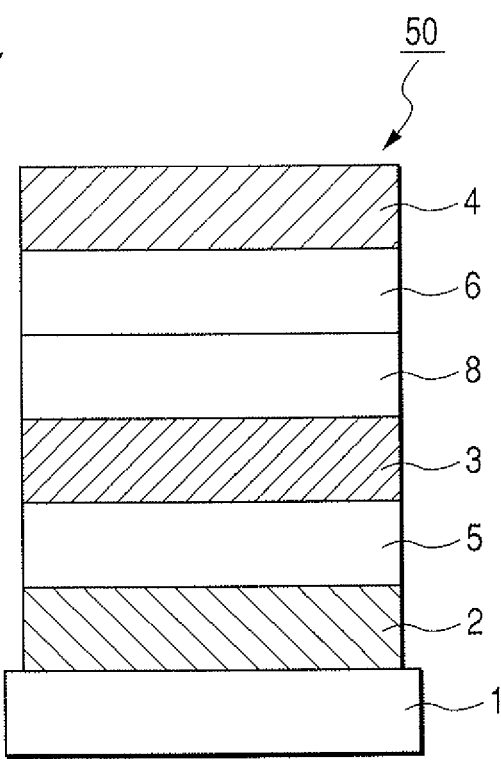
FIG. 5 is a sectional view showing a fifth embodiment in the organic light-emitting element of the present invention.

FIG. 5 is a sectional view showing a fifth embodiment of the organic light-emitting element of the present invention. The organic light-emitting element 50 as shown in FIG. 5 is one in which, in the organic light-emitting element 30 as shown in FIG. 3, a layer which prevents holes or excitons from escaping to the cathode 4 side (the hole/exciton blocking layer 8) is inserted between the light-emitting layer 3 and the electron transport layer 6. In this organic light-emitting element 50, a layer of an organic compound having a very high ionization potential is used as the hole/exciton blocking layer 8, thereby improving the luminous efficiency of the organic light-emitting element.

Figure 6:
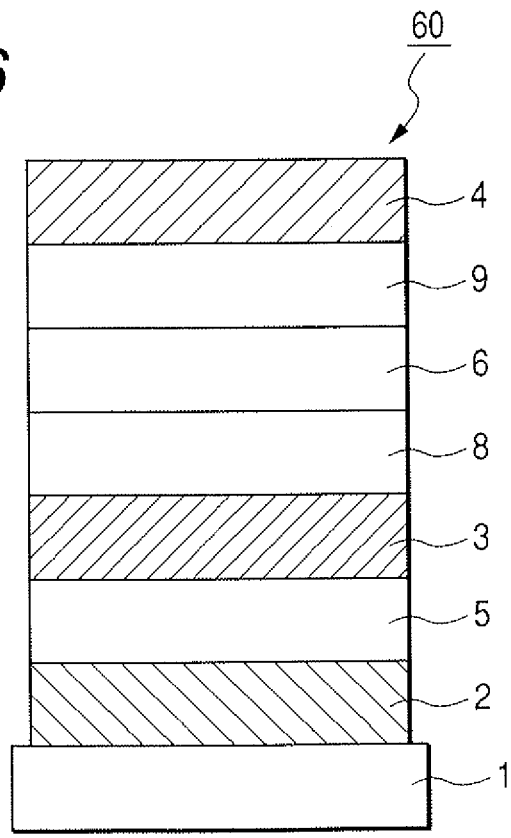
FIG. 6 is a sectional view showing a sixth embodiment in the organic light-emitting element of the present invention.

FIG. 6 is a sectional view showing a sixth embodiment of the organic light-emitting element of the present invention. The organic light-emitting element 60 as shown in FIG. 6 is one in which, in the organic light-emitting element 50 as shown in FIG. 5, the electron injection layer 9 is inserted between the cathode 4 and the electron transport layer 6. This organic light-emitting element 60 is improved in the adhesion between the cathode 4 and the electron transport layer 6 or the electron injection performance because the electron injection layer 9 is provided, and hence this is effective in reducing voltage.

It should be noted that FIGS. 1 to 6 present the very basic configurations of the organic light-emitting element, and the configuration of the organic light-emitting element using the biphenyl derivative of the present invention is by no means limited thereto. For example, various layer configurations may be adopted such that an insulating layer is provided at the interface between the electrode and the layer composed of an organic compound, an adhesive layer or an interference layer is provided, or the hole transport layer is made up of two layers different in ionization potential.

The biphenyl derivative of the present invention may be used in any embodiments shown in FIGS. 1 to 6. In this case, the biphenyl derivative of the present invention may be contained only in a single layer, or may be contained in a plurality of layers. Besides, the biphenyl derivative of the present invention which is contained in one layer may be of one type, or may be of two or more types.

The biphenyl derivative of the present invention is contained in any one of the layers composed of organic compounds, e.g., the light-emitting layer 3, the hole transport layer 5, the electron transport layer 6, the hole injection layer 7, the hole/exciton blocking layer 8 and the electron injection layer 9 which are shown in FIGS. 1 to 6. It is preferably contained in the light-emitting layer 3 or in the hole/exciton blocking layer 8. It is more preferably contained in the light-emitting layer 3.

The light-emitting layer 3 may be made up only of the biphenyl derivative of the present invention. It may preferably be made up of a host and a guest. In the case where the light-emitting layer is made up of a host and a guest, it is preferable that the host is the biphenyl derivative of the present invention, and the guest is a phosphorescent compound. Due to such a host-guest combination, it is possible to improve color purity, luminous efficiency and lifetime which are characteristic of the organic light-emitting element.

Here, the phosphorescent compound may include, but is not limited to, $Ir(ppy)_3$ and $Ir(piq)_3$.

Where the light-emitting layer is composed of a carrier transporting host and guest, the primary process leading to light emission includes the following some steps:
1. Transport of electrons and holes in the light-emitting layer.
2. Production of excitons by the host.
3. Transmission of excitation energy between host molecules.
4. Movement of excitation energy from the host to the guest.

The desired energy movement and light emission in the respective steps result from various deactivation steps and competition.

In order to improve the luminous efficiency of organic light-emitting elements, it is needless to say that a luminescent-center material itself must have a large luminous quantum yield. However, it greatly comes into question how efficiently the movement of energy takes place between the host and the host or between the host and the guest.

Accordingly, the biphenyl derivative of the present invention is used as a material making up either the charge transport layer or the light-emitting layer which makes up the organic light-emitting element, preferably as the host or guest of the light-emitting layer, and more preferably as the host of the light-emitting layer. Thus, the luminous efficiency of the element is improved, high luminance can be kept over a long period of time, and deterioration due to electrification can be reduced.

In the organic light-emitting element of the present invention, the biphenyl derivative of the present invention is used as a constituent of, in particular, the light-emitting layer. If necessary, a conventionally known low molecular type or polymer type hole transporting compound, luminescent compound or electron transporting compound may also be used together with the biphenyl derivative of the present invention.

The hole transporting compound may include aromatic tertiary amine compounds such as α-NPD and TPD.

The luminescent compound may include coumarine, quinacridone, rubrene and perylene.

The electron transporting compound may include BPhen, $Alq_3$, PBD and TPBi.

The material making up the anode may include ITO and IZO.

The material making up the cathode may include Al, Mg/Ag, ITO and KF.

As to the substrate used in the organic light-emitting element of the present invention, there are no particular limitations. Usable are opaque substrates such as substrates made of metals and substrates made of ceramics, and transparent substrates such as glass sheets, quartz sheets and plastic sheets.

A color filter film, a fluorescent color conversion filter film, a dielectric reflection film, etc. may also be used in the substrate to control luminescent color. A thin-film transistor (TFT) may further be formed on the substrate to make a connection therewith to set up the organic light-emitting element.

In regard to the direction in which light is to be sent out, both of the bottom emission in which light is taken out from the substrate side and the top emission in which light is taken out from the side opposite to the substrate may be employed.

A method for producing the organic light-emitting element of the present invention includes a vacuum deposition method, a spin coating method, a laminating method and an ink-jetting method.

EXAMPLES

The present invention is further described below in greater detail by giving Examples, to which the present invention is by no means limited.

Example 1

Synthesis of Exemplary Compound H-1

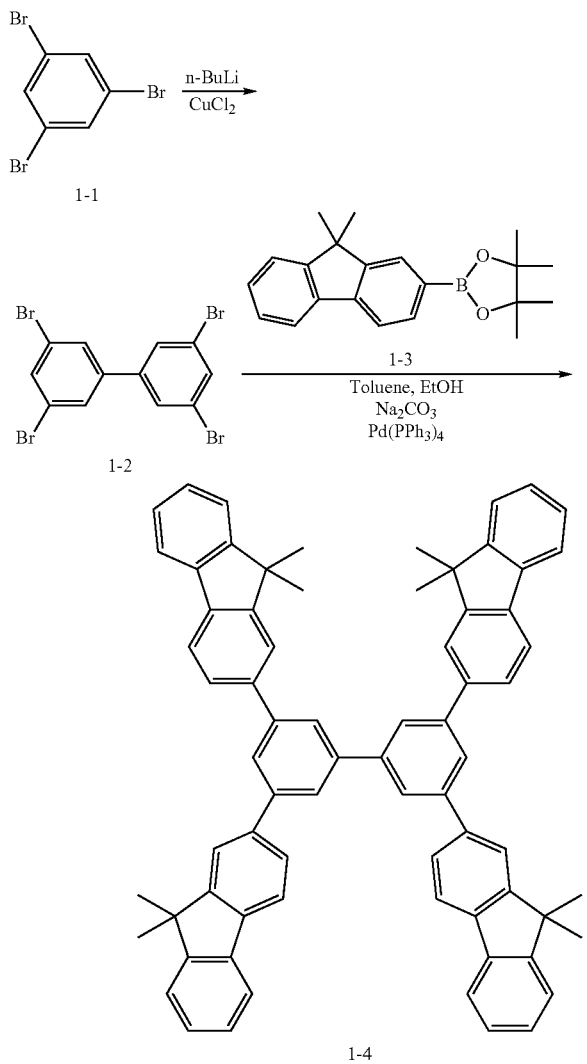

(1) First, 15.74 g (50 mmol) of 1,3,5-tribromobenzene (compound 1-1) was dissolved in 100 ml of dehydrated ether. Then, 34 ml (55 mmol) of a 1.60 M n-BuLi hexane solution was added dropwise over a period of 10 minutes at −78° C. in an atmosphere of nitrogen, followed by stirring for 10 minutes. Next, 7.39 g (55 mmol) of copper (II) chloride was added, followed by stirring for 30 minutes. The solution was then warmed to room temperature, and stirred for 2 hours. After the stirring, 100 ml of water was added, and the organic layer was extracted with chloroform, and then dried with anhydrous sodium sulfate. Thereafter, the solvent was distilled off under reduced pressure. Next, the resultant product was purified by recrystallization in a mixed solvent of chloroform and ethanol to produce 5.80 g of compound 1-2 (yield: 49.4%).

(2) Subsequently, the following compounds were dissolved in a mixed solvent of 55 ml of toluene, 28 ml of ethanol and 44 ml of a 2N sodium carbonate aqueous solution.
Compound 1-2: 1.53 g (3.25 mmol).
Compound 1-3: 6.41 g (20 mmol).

Next, while the resulting reaction mixture was stirred at room temperature in an atmosphere of nitrogen, 0.20 g (0.17 mmol) of tetrakis(triphenylphosphine)palladium(0) was added. Thereafter, the resultant reaction mixture was warmed to 75° C., and then stirred for 40 hours. After the stirring, the organic layer was extracted with chloroform, and then dried with anhydrous sodium sulfate. Thereafter, the solvent was distilled off under reduced pressure. After that, the resulting product was purified by recrystallization in toluene to produce 820 mg of Exemplary Compound H-1 (compound 1-4 (yield: 25.4%)).

MALDI-TOF MS (matrix-assisted laser desorption ionization time-of-flight mass spectrometry) ascertained 922.4 which is a M+ of this compound.

$^1$H-NMR measurement (400 MHz, CDCl$_3$) identified the structure of this compound by assignment of 58 protons thereof. The identification results were as follows:

(aryl: 7.97-7.31 ppm (m, 34H), methyl: 1.56-1.53 ppm (s, 24H).

Exemplary Compounds H-6, H-8, H-9, H-11, H-13, and H-21 can be synthesized in the same way as in Example 1 except that boronic acid derivatives shown in Table 1 below are substituted for the compound 1-3.

TABLE 1

| Compound to be synthesized | Boronic acid derivative |
|---|---|
| Exemplary Compound H-6 | |
| Exemplary Compound H-8 | |
| Exemplary Compound H-9 | |
| Exemplary Compound H-11 | |
| Exemplary Compound H-13 | |

TABLE 1-continued
| Compound to be synthesized | Boronic acid derivative |
|---|---|
| Exemplary Compound H-19 | 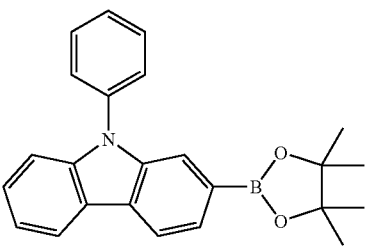 |
| Exemplary Compound H-21 | 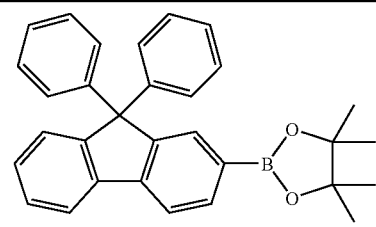 |
Example 2
Synthesis of Exemplary Compound H-42
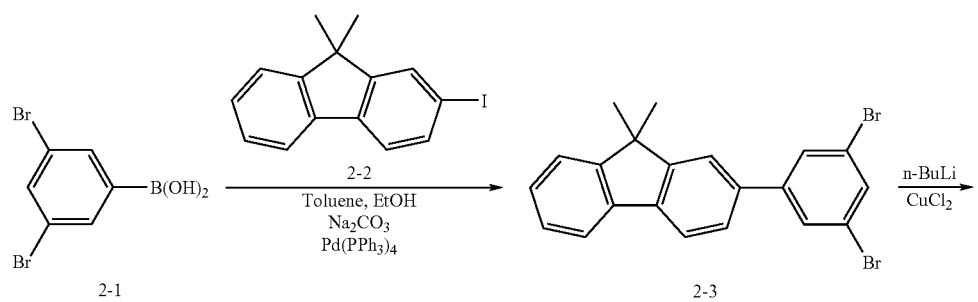
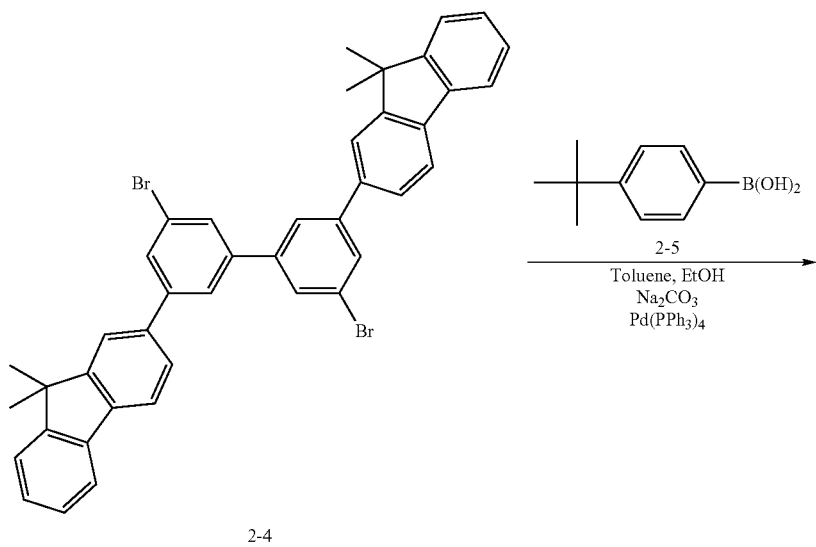

-continued

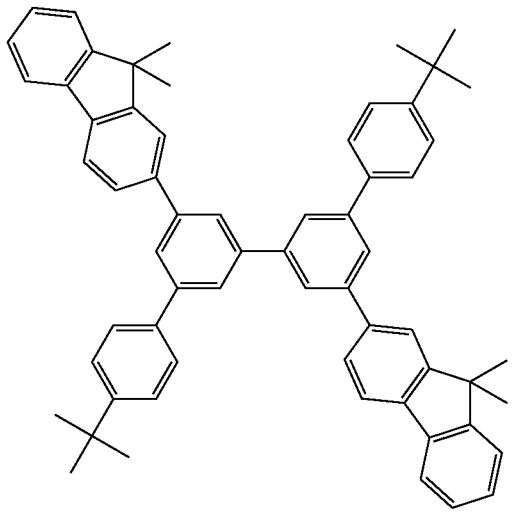

2-6

(1) Reagents shown below were dissolved in a mixed solvent of 5 ml of toluene, 50 ml of ethanol and 75 ml of a 2N sodium carbonate aqueous solution. 3,5-Dibromophenylboronic acid (compound 2-1: 5.10 g (18.2 mmol); and Compound 2-2: 17.51 g (54.7 mmol).

Next, while the resulting reaction mixture was stirred at room temperature in an atmosphere of nitrogen, 0.75 g (0.65 mmol) of tetrakis(triphenylphosphine)palladium(0) was added. After that, the resultant reaction mixture was heated to 75° C., and then stirred for 14 hours. After the reaction was completed, the organic layer was extracted with chloroform, and then dried with anhydrous sodium sulfate. Thereafter, the solvent was distilled off under reduced pressure. Next, the resulting product was purified by silica gel column chromatography (developing solvent: heptane) to produce 5.94 g of compound 2-3 (yield: 76.2%).

(2) Subsequently, 3.85 g (8.99 mmol) of the compound 2-3 was dissolved using 20 ml of dehydrated ether. Next, 6.5 ml (10.5 mmol) of a 1.60 M n-BuLi hexane solution was added dropwise over 10 minutes or more at −78° C. in an atmosphere of nitrogen, followed by stirring for 10 minutes. Thereafter, 1.35 g (10.1 mmol) of copper (II) chloride was added, followed by stirring for 30 minutes. Subsequently, the solution was then warmed to room temperature, and then stirred for 2 hours. After the stirring, 100 ml of water was added, and the organic layer was extracted with chloroform, and then dried with anhydrous sodium sulfate. Thereafter, the solvent was distilled off under reduced pressure. Next, the resultant product was purified by recrystallization in a mixed solvent of chloroform and ethanol to produce 1.25 g of compound 2-4 (yield: 39.9%).

(3) Subsequently, reagents shown below were dissolved in a mixed solvent of 7.0 ml of toluene, 3.5 ml of ethanol and 15 ml of a 2N sodium carbonate aqueous solution.

Compound 2-4: 1.00 g (1.43 mmol); and
Compound 2-5: 1.27 g (7.15 mmol).

Next, while the resulting reaction mixture was stirred at room temperature in an atmosphere of nitrogen, 0.10 g (0.087 mmol) of tetrakis(triphenylphosphine)palladium(0) was added. Thereafter, the resultant reaction mixture was heated to 75° C., and then stirred for 19 hours. After the stirring, the organic layer was extracted with chloroform, and then dried with anhydrous sodium sulfate. Then, the solvent was distilled off under reduced pressure. Next, the resulting product was purified by recrystallization in toluene to produce 480 mg of Exemplary Compound H-42 (compound 2-6 (yield: 41.8%)).

MALDI-TOF MS (matrix-assisted laser desorption ionization time-of-flight mass spectrometry) ascertained 802.4 which is a M+ of this compound.

$^1$H-NMR measurement (400 MHz, CDCl$_3$) identified the structure of this compound by assignment of 58 protons thereof. The identification results were as follows:

(aryl: 7.93-7.31 ppm (m, 28H), methyl: 1.55-1.54 ppm (s, 12H), methyl: 1.39 ppm (s, 18H).

Exemplary Compounds H-3, H-4, H-5, H-10, H-14, H-15, H-17, H-18, H-22, H-23, H-43, H-44, H-45 and H-48 can be synthesized in the same way as in Example 2 except that halogen compounds shown in Tables 2 and 3 below are substituted for the compound 2-2 in step (1) of Example 2 and boronic acid derivatives shown in Tables 2 and 3 below are substituted for the compound 2-5 in step (3) of Example 2.

TABLE 2
| Compound to be synthesized | Halogen compound | Boronic acid derivative |
|---|---|---|
| Exemplary Compound H-3 | 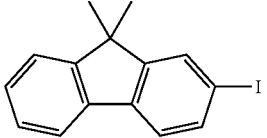 | 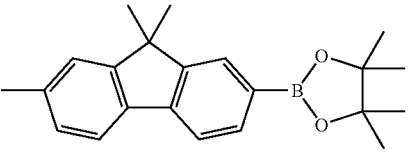 |
| Exemplary Compound H-4 | 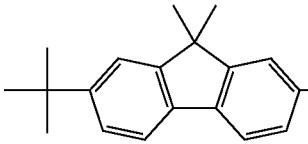 | 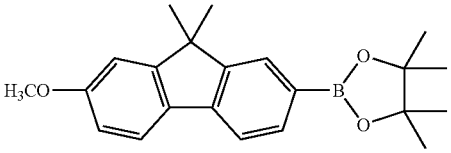 |
| Exemplary Compound H-5 | 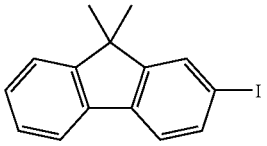 | 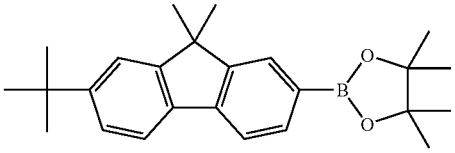 |
| Exemplary Compound H-10 | 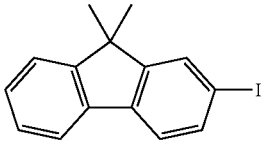 | 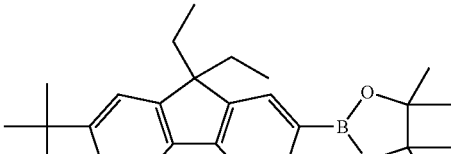 |
| Exemplary Compound H-14 | 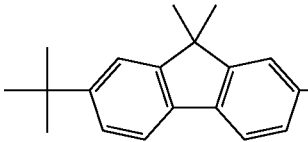 | 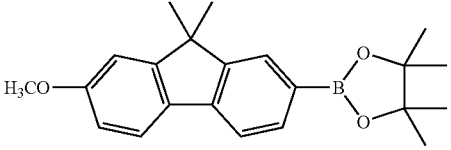 |
| Exemplary Compound H-15 | 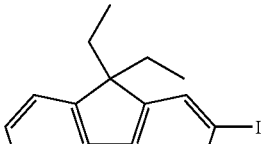 | 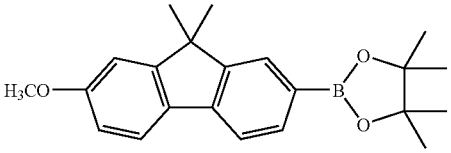 |
| Exemplary Compound H-17 | 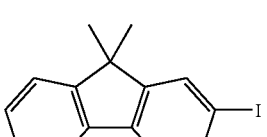 | 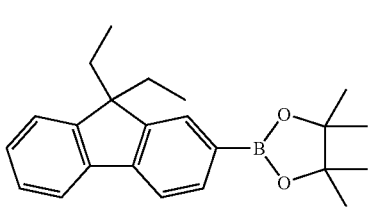 |
| Exemplary Compound H-18 | 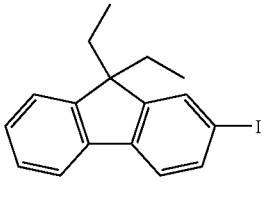 | 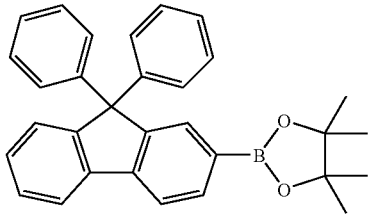 |

TABLE 2-continued

| Compound to be synthesized | Halogen compound | Boronic acid derivative |
| --- | --- | --- |
| Exemplary Compound H-22 | 9,9-dimethyl-2-iodofluorene | N-phenyl-carbazole-2-boronic acid pinacol ester |
| Exemplary Compound H-23 | 9,9-dimethyl-2-iodofluorene | N-methyl-carbazole-2-boronic acid pinacol ester |
| Exemplary Compound H-43 | 9,9-dimethyl-2-iodofluorene | phenylboronic acid pinacol ester |

TABLE 3

| Compound to be synthesized | Halogen compound | Boronic acid derivative |
| --- | --- | --- |
| Exemplary Compound H-44 | iodobenzene | 2-(9,9-dimethylfluoren-2-yl)-N-carbazolyl-boronic acid pinacol ester |
| Exemplary Compound H-45 | 7-tert-butyl-2-iodo-9,9-dimethylfluorene | 4-tert-butylphenylboronic acid pinacol ester |
| Exemplary Compound H-48 | 1-bromopyrene | 9,9-dimethylfluorene-2-boronic acid pinacol ester |

Example 3

Production of Organic Light-emitting Element

The organic light-emitting element having such a structure as shown in FIG. 3 was produced in the following way.

On a glass substrate (the substrate 1), a indium-tin oxide (ITO) film was formed as the anode 2 by sputtering in a layer thickness of 120 nm, and was subjected to ultrasonic cleaning successively with acetone and isopropyl alcohol (IPA), and then boiling cleaning with IPA, followed by drying, and was subsequently subjected to UV/ozone cleaning. The substrate with the ITO film thus treated was used as a transparent conductive support substrate.

Next, as the hole transport layer 5, a film of Compound A represented by the following formula was formed by vacuum deposition in a layer thickness of 30 nm. In this case, during the vacuum deposition, the degree of vacuum was set at $1.0 \times 10^{-4}$ Pa and the rate of film formation was set at 0.1 nm/sec.

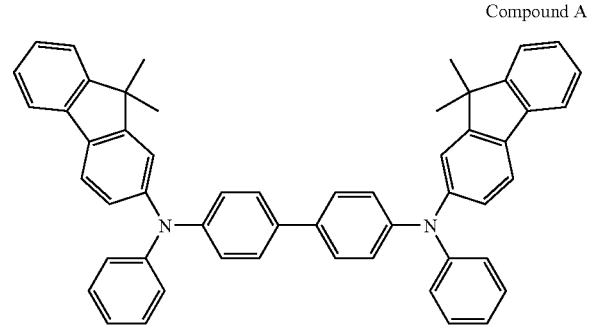

Compound A

Next, Exemplary Compound H-1 to be a host and Compound B represented by the following formula to be a guest were co-deposited on the hole transport layer 5 to form the light-emitting layer 3 so that Compound B was in a content of 10% by mass based on the whole mass of the light-emitting layer 3. In this case, the light-emitting layer was formed in a layer thickness of 50 nm. During the vacuum deposition, the degree of vacuum was set at $1.0 \times 10^{-4}$ Pa and the rate of film formation was set at 0.1 nm/sec.

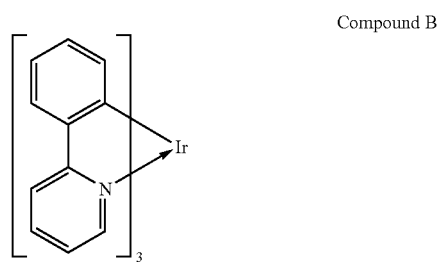

Compound B

Next, bathophenanethroline (BPhen) was deposited to form the electron transport layer 6 having a thickness of 40 nm. In this case, during the vacuum deposition, the degree of vacuum was set at $1.0 \times 10^{-4}$ Pa and the rate of film formation was set at 0.2 nm/sec to 0.3 nm/sec.

Next, potassium fluoride was deposited on the above organic layer by vacuum deposition to form a film having a thickness of 0.5 nm, and then an aluminum film was formed thereon by vacuum deposition in a thickness of 150 nm. In this case, during the vacuum deposition, the degree of vacuum was set at $1.0 \times 10^{-4}$ Pa and the rate of film formation was set at 1.0 nm/sec to 1.2 nm/sec. The aluminum-potassium fluoride composite film thus formed functions as an electron injection electrode (the electrode 4).

Next, in order for the element obtained as above not to deteriorate due to adsorption of water, it was covered with a protective glass sheet in an atmosphere of dry air and then sealed with an acrylic resin type adhesive. Thus, an organic light-emitting element was obtained.

To the organic light-emitting element thus obtained, a voltage was applied setting the ITO electrode (anode 2) to be a positive pole and the Al electrode (cathode 2) to be a negative pole. As a result, it was confirmed that green light was emitted.

The organic light-emitting element shown in FIG. 3 can be produced in the same manner as in Example 3 except that Compound C shown below is substituted for Compound B as the guest of the light-emitting layer 3.

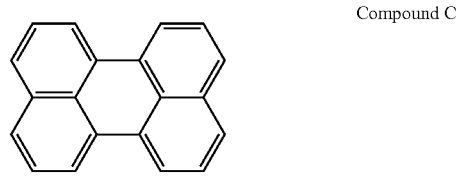

Compound C

The organic light-emitting element shown in FIG. 5 can be produced in the same manner as in Example 3 except that Exemplary Compound H-5 is substituted for Exemplary Compound H-1 as the host of the light-emitting layer 3 and further that, between the light-emitting layer 3 and the electron transport layer 6, Exemplary Compound H-1 is deposited to form the hole blocking layer 8.

Examples 4 to 8

Organic light-emitting elements were produced in the same manner as in Example 3 except that each of the compounds shown in Table 3 below was used in place of Exemplary Compound H-1 as the host of the light-emitting layer 3. The organic light-emitting elements obtained were evaluated in the same manner as in Example 3. As a result, it was confirmed that light was emitted.

TABLE 4

|  | Host |
| --- | --- |
| Example 4 | Exemplary Compound H-6 |
| Example 5 | Exemplary Compound H-9 |
| Example 6 | Exemplary Compound H-23 |
| Example 7 | Exemplary Compound H-42 |
| Example 8 | Exemplary Compound H-43 |

Thus, the organic light-emitting element using the biphenyl derivative of the present invention afforded highly efficient light emission at a low applied voltage. The organic light-emitting element of the present invention is also superior in durability.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-101489, filed Apr. 9, 2007, which is hereby incorporated by reference herein its entirety.

What is claimed is:

1. A biphenyl derivative represented by the following general formula (1):

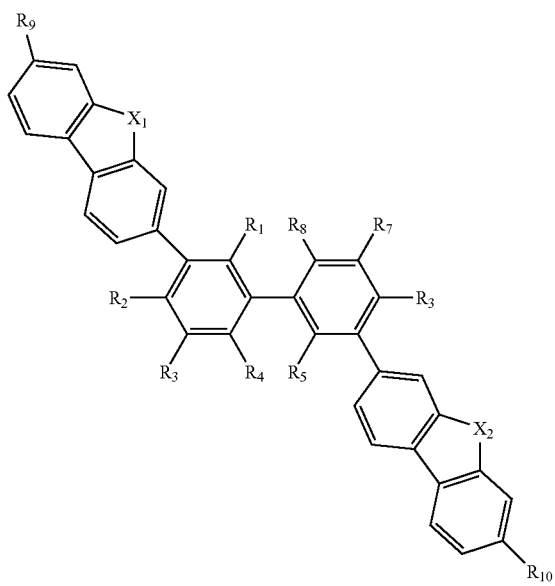

wherein $R_1$, $R_2$, $R_4$ to $R_6$ and $R_8$ to $R_{10}$ each independently represent a hydrogen atom, a substituted or unsubstituted alkyl group, a substituted or unsubstituted aralkyl group, a substituted or unsubstituted alkenyl group, a substituted or unsubstituted alkynyl group or a substituted or unsubstituted alkoxyl group; $R_3$ and $R_7$ each independently represent a hydrogen atom, a substituted or unsubstituted alkyl group or a substituted or unsubstituted aryl group; and $X_1$ and $X_2$ each independently represent —$CR_{11}R_{12}$—, wherein $R_{11}$ and $R_{12}$ each independently represent a hydrogen atom, an alkyl group, a substituted or unsubstituted aralkyl group, a substituted or unsubstituted aryl group, a substituted or unsubstituted heterocyclic group or a halogen atom.

2. An organic light-emitting element which comprises:
an anode and a cathode; and
a layer containing an organic compound, held between the anode and the cathode;
the layer containing an organic compound comprising the biphenyl derivative according to claim 1.

3. The organic light-emitting element according to claim 2, wherein the biphenyl derivative is contained in a light-emitting layer.

4. The organic light-emitting element according to claim 2, wherein the light-emitting layer comprises a host and a guest, and the host is the biphenyl derivative.

5. The organic light-emitting element according to claim 4, wherein the guest is a phosphorescent compound.

\* \* \* \* \*